(12) United States Patent
Schulz et al.

(10) Patent No.: US 12,371,651 B2
(45) Date of Patent: Jul. 29, 2025

(54) BIOREACTOR OR FERMENTER FOR THE CULTURING OF CELLS OR MICROORGANISMS IN SUSPENSION IN INDUSTRIAL SCALE

(71) Applicant: Boehringer Ingelheim International GmbH, Ingelheim am Rhein (DE)

(72) Inventors: Torsten Wilhelm Schulz, Biberach an der Riss (DE); Thomas Wucherpfennig, Ulm (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 318 days.

(21) Appl. No.: 17/766,880

(22) PCT Filed: Oct. 5, 2020

(86) PCT No.: PCT/EP2020/077797
§ 371 (c)(1),
(2) Date: Apr. 6, 2022

(87) PCT Pub. No.: WO2021/069353
PCT Pub. Date: Apr. 15, 2021

(65) Prior Publication Data
US 2024/0101950 A1    Mar. 28, 2024

(30) Foreign Application Priority Data
Oct. 9, 2019 (EP) ..................... 19202145

(51) Int. Cl.
*C12M 1/34* (2006.01)
*C12M 1/00* (2006.01)
*C12M 1/06* (2006.01)
(52) U.S. Cl.
CPC ............ *C12M 41/34* (2013.01); *C12M 27/02* (2013.01); *C12M 29/06* (2013.01)

(58) Field of Classification Search
CPC ...... C12M 41/34; C12M 27/02; C12M 29/06; C12N 5/0655; C12N 2501/115;
(Continued)

(56) References Cited

U.S. PATENT DOCUMENTS

| 5,994,567 A | 11/1999 | Kingsley et al. |
| 8,894,756 B2 | 11/2014 | Galliher et al. |

(Continued)

FOREIGN PATENT DOCUMENTS

| CN | 201678670 U | 12/2010 |
| CN | 104073430 A | 10/2014 |

(Continued)

OTHER PUBLICATIONS

Birch et al., "The Influence of Sparger Design and Location on Gas Dispersion in Stirred Vessels", Chemical Engineering Research and Design, Jul. 1, 1997, vol. 75, No. 5, pp. 487-496.
(Continued)

*Primary Examiner* — Michael L Hobbs
(74) *Attorney, Agent, or Firm* — Shelley A. Jones

(57) ABSTRACT

The present disclosure is directed to a bioreactor or fermenter for the culturing of cells or microorganisms in suspension in a liquid medium in industrial scale comprising a vessel containing the culture in a liquid medium having a determined filling height; a stirrer provided in the vessel to stir the liquid medium; a first sparger arranged in the bottom portion of the vessel; and a second or optional more spargers provided above the first sparger to supply additional air bubbles and/or additional oxygen gas bubbles continuously to the liquid medium whereby the second sparger is located at a position in the bioreactor or fermenter above the first sparger in a predefined distance η. It is also described a process for the independent management of dissolved $CO_2$ and $O_2$, by selecting a suitable modified gas flow rate $q_{mod}$.

18 Claims, 13 Drawing Sheets

(58) Field of Classification Search
CPC ............ C12N 2501/15; C12N 2506/13; C12N 2506/1307; C12N 2513/00
See application file for complete search history.

(56) References Cited

U.S. PATENT DOCUMENTS

| | | | |
|---|---|---|---|
| 2007/0065927 A1* | 3/2007 | Brahmbhatt | B01F 23/233 |
| | | | 435/101 |
| 2008/0233631 A1 | 9/2008 | Higashiyama | |
| 2010/0093050 A1 | 4/2010 | Hakalehto | |
| 2013/0078689 A1* | 3/2013 | Hickey | C12P 7/52 |
| | | | 435/141 |
| 2013/0078693 A1* | 3/2013 | Hickey | C12M 29/06 |
| | | | 435/161 |
| 2016/0190038 A1 | 6/2016 | Koyama et al. | |

FOREIGN PATENT DOCUMENTS

| | | |
|---|---|---|
| CN | 203855575 U | 10/2014 |
| CN | 107619777 A | 1/2018 |
| EP | 0099634 A2 | 2/1984 |
| JP | 2001231544 A | 8/2001 |
| JP | 2008182899 A | 8/2008 |
| JP | 2012517217 A | 8/2012 |
| JP | 2019520065 A | 7/2019 |
| WO | 0233048 A1 | 4/2002 |
| WO | 2008088371 A2 | 7/2008 |
| WO | 2010089151 A1 | 8/2010 |
| WO | 2017207822 A1 | 12/2017 |

OTHER PUBLICATIONS

Gray et al., "CO2 in large-scale and high-density CHO cell perfusion culture", Cytotechnology, 1996, vol. 22, pp. 65-78.
International Search Report and Written Opinion for corresponding application, PCT/EP2020/077797, date of mailing Jan. 20, 2021.
Klaas Van't Riet, "Review of Measuring Methods and Results in Nonviscous Gas-Liquid Mass Transfer in Stirred Vessels", Ind. Eng. Chem. Process, 1979, vol. 18, No. 3, pp. 357-364.
Leigh, "Frequency response methods", 2004, Chapter 5.
Rewatkar et al., "Role of sparger design on gas dispersion in mechanically agitated gas-liquid contactors", Canadian Journal of Chemical Engineering, Apr. 1993, vol. 71, No. 2, pp. 278-291.
Sardeing et al., "Gas-Liquid Mass Transfer", Chemical Engineering Research and Design, Sep. 1, 2004, vol. 82, No. 9, pp. 1161-1168.
Sen Xu et al., "A practical approach in bioreactor scale-up and process transfer using a combination of constant P/V and vvm as the criterion", Biotechnology Progress, May 14, 2017, vol. 33, No. 4, pp. 1146-1159.
Sieblist et al., "Insights into large-scale cell-culture reactors: II. Gas-phase mixing and CO2 stripping", Biotechnology Journal, 2011, vol. 6, pp. 1547-1556.
Wachi et al., "Gas-Phase Dispersion in Bubble Columns", Chemical Engineering Science, 1990, vol. 45, No. 4, pp. 901-905.
Manatos et al., "RTD studies in an industrial flotation column: use of the radioactive tracer technique", International Journal of Mineral Processing, 1992, vol. 36, pp. 81-91.
Abstract in English for CN104073430, Oct. 1, 2014.
Abstract in English for JP2001231544.

* cited by examiner

BIOREACTOR OR FERMENTER FOR THE CULTURING OF CELLS OR MICROORGANISMS IN SUSPENSION IN INDUSTRIAL SCALE

TECHNICAL FIELD

The invention relates to a bioreactor or fermenter for the culturing of cells or microorganisms in suspension in industrial scale.

BACKGROUND OF THE INVENTION

In biopharmaceutical processes it is always of special interest to arrive at an industrial scale. Frequently the increasing extent of the bioreactor volume results in a decreasing cell performance of the cells to be cultivated, since the maintenance of the culturing conditions often limits the possibility to perform large scale culturing. In addition to the production on a large scale, the quality standards of the manufactured products must be fulfilled and a reliable capacity for supplying the market at the same time has to be provided. It is therefore always a concern to reduce or eliminate the size-dependency of the cell cultivating performance in order to achieve a consistent high product titer and a high product yield. As expected, a higher capacity utilisation of the provided increased bioreactor or fermenter volume will result in an improved productivity.

For the cultivation of cells it is of vital significance to ensure ideal growth conditions. In this regard it is of importance to maintain a favourable physicochemical environment such as a desired dissolved oxygen content, culture pH value, temperature and the like. However, cells are known to metabolically respond to their environment. Especially concentration gradients can inhibit the cell growth of cells in large-scale bioreactors. Furthermore, for example, the pH value has a significant influence on the surrounding medium. In a stirred bioreactor or fermenter metabolically active cells secrete $CO_2$ which dissolves in the surrounding liquid medium and absorb $O_2$ from their environment to complete the cell respiration. For example, the following reaction of $CO_2$ in a liquid medium can be observed (pH<8.0):

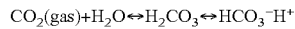

$$CO_2(gas) + H_2O \leftrightarrow H_2CO_3 \leftrightarrow HCO_3^- H^+$$

Therefore, the entry of $CO_2$ into the liquid phase of a bioreactor or fermenter will lead to an acidic milieu due to the lowering of the pH value. Reversely, the outgassing of $CO_2$ will rise the pH value. It is therefore an usual measure to provide oxygen gas to a bioreactor or fermenter via a gas supply or gas supplying unit called "sparger".

Therefore, in general, to achieve high product qualities and efficiencies, a constant oxygen supply as well as a well-defined depletion of dissolved carbon dioxide by so called ($CO_2$-)stripping has to be ensured. This should be possible for any size of bioreactor or fermenter to enable a reliable scale up for any cell or microorganism to be cultivated.

A conventional gas supplying unit in a bioreactor or fermenter causes gas bubbles to enter into the liquid phase, initially consisting of pure $O_2$, in case pure $O_2$ is used, as gas supply. During the stay and rise of the bubbles in the cell or microorganism containing reactor $O_2$ passes over from the gas phase into the liquid phase (reaction (1)) and vice versa $CO_2$ formed in a metabolic reaction passes over from the liquid phase into the gas phase i.e. into the bubble (reaction (2)). Due to Henry's law constant (as defined e.g. by Christian Sieblist et al., Insights into large-scale cell-culture reactors: II. Gas-phase mixing and $CO_2$ stripping, Biotechnol. J. 2011, 6, 1547-1556) the transfer of $O_2$ and $CO_2$, respectively, takes place at different rates.

By way of illustration, the processes and reactions in question which take place in a bioreactor or fermenter are shown in FIG. 1. FIG. 1 exemplifies the distribution of dissolved $CO_2$ in a schematic bioreactor or fermenter having a gas supply providing, for example, pure $O_2$ at the bottom and close to a stirrer (not shown). The bubble 10 illustrated in FIG. 1 is shown in 3 different conditions while ascending in the liquid, namely as starting naïve bubble 10.1, in the middle section as bubble 10.2 and in the upper section of the bioreactor or fermenter as bubble 10.3. Therefore, starting from the gas supply at the lower part of the bioreactor the $O_2$ containing bubble 10.1 begins the rising up to the surface in the liquid medium. In the middle section of FIG. 1 the processes and reactions which occur are schematically shown: $O_2$ gas passes over from the bubble 10.2 into the liquid phase (reaction (1)) and $CO_2$ gas passes over from the liquid phase into the bubble 10.2 (reaction (2)). The Henry's law constants for the $O_2$ gas and $CO_2$ gas, respectively, are significantly different (Sieblist et al.; loc.cit.). When measured under the same conditions the value for $O_2$ is about 0.0013 mol/(kg*bar) and for $CO_2$ about 0.034 mol/(kg*bar); i.e. about 25-fold higher, viz. the value for $CO_2$ is larger so that an accelerated diffusion occurs. Therefore, the rate of reaction (2) is much faster compared with the rate of reaction (1) (which is illustrated in FIG. 1 with the different thickness of the arrows). Since Henry's constant for $CO_2$ is higher than the corresponding value for $O_2$, the carbon dioxide concentration of the bubble increases more quickly on its way through the reactor than the value for $O_2$ decreases. The consequence is that the driving force for the $CO_2$ mass transfer is decreasing during the bubble rise.

In fact, the bubble 10 can supply oxygen to the liquid phase for minutes, but its carbon dioxide uptake stops due to $CO_2$ saturation within seconds. When the bubble is saturated with $CO_2$, it no longer takes up $CO_2$. This is shown with bubble 10.3 in FIG. 1. After some seconds, while the bubble 10.3 still provides oxygen to the culture, it has no further capacity to take up $CO_2$. Hence, the bubble provided in the liquid medium of the bioreactor is only part-time-active for $CO_2$ stripping. Thus, the bubble reaches the saturation concentration of $CO_2$ after a specific ascending height within the bioreactor or fermenter. Therefore, in the upper part of FIG. 1 the bubble 10.3 does no longer absorb $CO_2$ gas but only $O_2$ gas passes over from the bubble 10.3 into the liquid phase. As a result, from the lower part to the upper part of FIG. 1, from the bubble in condition 10.1 via condition 10.2 to condition 10.3, the delivery of $O_2$ into the liquid medium decreases while the concentration of $CO_2$ in the bubble increases until the saturation concentration is reached. This is schematically illustrated in the triangle shaped arrows at the right side of FIG. 1: arrow (3) from the broad part to the arrowhead symbolizes that the relative delivery tendency of $O_2$ to the culture medium, i.e. from the gas phase into the liquid phase, is decreasing. Arrow (4) in FIG. 1 symbolizes the increasing saturation of the bubble with $CO_2$, from the arrowhead to the broad part, whereby $CO_2$ passing over from the liquid phase into the gas phase which proceeds much faster than the delivery of $O_2$. The square (5) illustrates the region where no more uptake of solved $CO_2$ is possible from the liquid phase into the bubble 10.3 because the bubble 10.3 has reached the saturation concentration of $CO_2$.

Thus, after a very short time the bubble 10.3 is saturated with $CO_2$ gas and it is no longer able to take up more $CO_2$ from the liquid phase, but the bubble 10.3 may still release $O_2$ gas into the liquid environment. In a bioreactor or fermenter where a gas supply is permanently provided a whole series of bubbles are provided which enter the liquid phase and contribute to a gradient of $CO_2$ within the liquid phase. In the lower part the bubbles have the ability to take up $CO_2$, an ability which gets more and more lost in the course of the ascending of the bubbles to the top.

Particularly in large production bioreactors or fermenters, $CO_2$ removal from the culture is known to be a major problem because stripping is mainly affected by the change of the gas composition of the bubbles during their movement through the bioreactor or fermenter from the gas supply system towards the top.

Therefore, as explained above, the management of the $O_2$- and $CO_2$-concentration is of special interest in biopharmaceutical processes, particularly large-scale biopharmaceutical processes. In order to develop a strategy which allows the improvement of the control and adjustment of the stripping of $CO_2$ for large-scale systems, the oxygen and carbon dioxide mass transfer performance has to be evaluated in detail. The parameter which is to be observed in connection with the $CO_2$ gas is the (volumetric) carbon dioxide mass transfer coefficient $k_L a_{CO2}$, wherein $k_L$ is the transport coefficient for $CO_2$ and a is the specific interfacial area, whereby $a=A/V_L$, i.e. the total mass transfer cross section A per culture volume $V_L$ (cf. Christian Sieblist et al., loc.cit.). The parameter which is to be observed in connection with the $O_2$ gas is the (volumetric) oxygen mass transfer coefficient $k_L a_{O2}$. The mass transfer coefficient may be based on the volume and is then the volumetric mass transfer coefficient.

Furthermore, on one hand, an excessive concentration level of dissolved $CO_2$ has to be avoided and $CO_2$ needs to be stripped off. Insufficient $CO_2$-stripping in large bioreactors or fermenters (i.e. those with large heights and thus long distances for the bubbles to ascend) often results in an accumulation of dissolved $CO_2$, leading to a high concentration of $CO_2$ in the liquid phase which inhibits cell growth and product formation. On the other hand, carbon dioxide is needed for synthesis of nucleic acids and its amount must not be too small. Therefore, it should be kept in mind that the stripping of $CO_2$ shall not have any negative effect on the cells or microorganisms to be cultivated.

Consequently, a strategy has to be developed which enhances and allows to control and adjust the carbon dioxide mass transfer coefficient $k_L a_{CO2}$ for a large-scale system without affecting the oxygen mass transfer coefficient $k_L a_{O2}$ significantly.

In order to examine and elucidate the interrelations of $CO_2$ and $O_2$ mass transfers we have performed various studies to identify the influence of different operation conditions. Particularly, the mixing efficiency and mass transfer performance of $CO_2$ on laboratory scale and industrial scale have been examined in detail. The results are summarized in FIGS. 2 and 3.

FIGS. 2 and 3 show the volumetric mass transfer coefficient for carbon dioxide $k_L a_{CO2}$ in dependency of the volumetric stirrer power input P/V in two different volumes for different manually given superficial gas velocities $w^0_g$ on laboratory scale and industrial scale, respectively. Specifically, FIG. 2 shows the experiments on laboratory scale in an aerated stirred bioreactor or fermenter having a volume of 2 L (height in cm range); FIG. 3 shows the experiments on industrial scale in an aerated stirred bioreactor or fermenter having a volume of 12,000 L (height in m range).

As may be expected, FIGS. 2 and 3 show that the volumetric mass transfer coefficient for carbon dioxide $k_L a_{CO2}$ increases in the same extent as the superficial gas velocity $w^0_g$ increases, in both experiments, namely in laboratory scale as well as in industrial scale. Further, it was found, that the mass transfer performance for carbon dioxide is significantly different on laboratory scale compared to the industrial scale process. It was unexpected, however, that the volumetric stirrer power input has a significant impact on the laboratory scale but a minimal impact on the industrial scale. As may be seen from FIGS. 2 and 3 the volumetric mass transfer coefficient $k_L a_{CO2}$ for the industrial scale reactor is up to ten times lower compared to the laboratory scale reactor.

In order to better illustrate the difference between the laboratory and industrial scale experiments it is referred to FIG. 4 wherein the comparison of the mass transfer coefficient for carbon dioxide $k_L a_{CO2}$ between laboratory and industrial scales is shown. FIG. 4 shows the relative influence of the specific power input on the volumetric carbon dioxide mass transfer coefficient compared to the volumetric mass transfer coefficient measured at a volumetric power input P/V=21 W m$^{-3}$. In comparison of the volumetric carbon dioxide mass transfer coefficient $k_L a_{CO2}$ between laboratory and industrial scale, it gets obvious that the mass transfer performance cannot be enhanced significantly with increasing volumetric power input P/V for the industrial scale, whereas on laboratory scale the mass transfer performance for $CO_2$ can be enhanced by up to 70% from 21 to 168 W m$^{-3}$. Therefore, FIG. 4 demonstrates an increase of +70% of the $k_L a_{CO2}$ with increasing stirrer input in laboratory scale (2 L system), whereas in industrial scale only a +5% increase of the $k_L a_{CO2}$ can be observed (12,000 L system).

Therefore, it becomes evident for the industrial scale bioreactor or fermenter based on FIGS. 2 to 4 that the mass transfer performance for $CO_2$ cannot be enhanced significantly with increasing volumetric power input P/V, whereas on a laboratory scale the mass transfer performance for $CO_2$ can be enhanced by up to 70% (cf. FIG. 4).

The different behaviour of the two systems can be basically explained by the residence time of the gaseous phase within the systems, as already explained above. On industrial scale, the equilibrium of the $CO_2$-concentration between bubble and liquid is reached far before the bubble is reaching the surface whereas on laboratory scale the residence time is too short to reach equilibrium. Therefore, enhancing the interfacial area with increasing stirrer frequency leads to higher mass transfer coefficients on laboratory scale whereas on large scale the stronger dispersion of "dead bubbles" (i.e. those with $CO_2$ saturation) is useless.

In case of oxygen mass transfer, further experiments have shown that even on industrial scale the equilibrium is not reached. Therefore, the higher the volumetric power input the higher the interfacial area and therefore the higher the volumetric mass transfer coefficient $k_L a_{O2}$. Therefore, it is concluded that the volumetric mass transfer coefficient for carbon dioxide can only be enhanced significantly with higher gas flow rates, but not with a higher volumetric power input.

The difficulties in stripping of carbon dioxide on industrial scale is mostly related to the fact that the gaseous phase is already saturated with carbon dioxide only shortly above the submersed gas supply provided on or near the bottom of the bioreactor or fermenter. Thus, the apparently most feasible option to increase the mass transfer performance for carbon dioxide is to increase the gas flow rate. However, this leads to an often unwanted increase of the oxygen mass transfer rate as well and therefore an independent management of the $O_2$- and $CO_2$-concentration within the bioreactor or fermenter is not possible.

In prior art, reactors having two spargers are already known and commercially available. For example, in EP 0 099 634 A2 it is described a reactor apparatus for multiphase contacting between gas, solid and liquid phases comprising a cylindrical vessel, a draft tube, a conical bottom and a gas-sparger system. A gas sparger 16 is located at the lower end of the vessel and in the gap between the inner wall and the conical surface perimeter for admitting at least one gas in bubble form into a continuous liquid phase in which particulate solid phase is suspended contained in the vessel. An auxiliary gas sparger in form of a ring sparger 34 surrounds the draft tube and is constructed to eject gas in bubble form radially outwardly thereof into the liquid phase. EP 0 099 634 A2 is completely silent with regard to the distance between the two spargers.

In WO 2002/33048 A1 it is disclosed a method of culturing a microorganism under aerobic conditions in a fermentation vessel comprising the injection of a first oxygen-containing gas into the lower portion of the vessel in a heterogeneous flow causing a chaotic motion of the broth and the introduction of a second oxygen-containing gas in the vessel characterised by introducing the second oxygen-containing gas as a heterogeneous flow of gas bubbles moving in the vessel in all possible directions, independently of the direction of the flow of the broth resulting in turbulent flow conditions at the site of injection; and as a set of gas bubbles of non-uniform size and a wide size distribution. The distance between the two spargers is not mentioned and not critical because there are no limitations for the inlet position of the second oxygen-containing gas stream as outlined on page 4, I. 20-24 of the description.

In Sen Xu et al.: "A practical approach in bioreactor scale-up and process transfer using a combination of constant P/V and vvm as the criterion", Biotechnology Progress, Vol. 33, No. 4, 2017, pp. 1146-1159, the bioreactor scale-up as a critical step in the production of therapeutic proteins such as monoclonal antibodies (MAbs) is evaluated. For example, the sparger $k_La$ and $k_La_{CO2}$ ($CO_2$ volumetric mass transfer coefficient) from a range of bioreactor scales (3-2,000 L) with different spargers is examined. In this relation a single and a dual sparger system are described without any disclosure about the geometry thereof. Typically, in a dual sparger system both spargers are at roughly the same position and not at different heights.

Furthermore, U.S. Pat. No. 5,994,567 from the field of organic chemistry is directed to direct oxygen injection into bubble column reactors, i.e. a liquid phase oxidation process, wherein a first oxygen-containing gas is injected into the lower portion of a bubble column reactor vessel containing an oxidizeable organic liquid. A second oxygen-containing gas is further injected into the reactor at a point or points wherein the liquid is substantially depleted in dissolved oxygen prior to said injection. Oxygen from both the first and second oxygen-containing gases is used to oxidize the organic liquid such as cumene or cyclohexane. Therefore, it is not described a stirred tank bioreactor or fermenter for the culturing of cells or microorganisms but a chemical reaction whereby the stripping of $CO_2$ produced by cultivated, living cells is not of any importance.

The disclosure of WO 2008/088371 A2 concerns systems for containing and manipulating fluids including systems and methods involving supported collapsible bags that may be used as reactors for performing chemical, biochemical and/or biological reactions. In one aspect, fluids contained in a vessel can be sparged, e.g., such that a fluid is directed into a container of the vessel, and in some cases, the sparging can be controlled by rapidly activating or altering the degree of sparging as needed. It is mentioned that multiple spargers may be used in some cases. However, the document is silent on specific geometric arrangements of those. The different spargers 47 or 301 as described are according to FIG. 1 located at the same height at the bottom of the reactor, yet without a specific teaching related to the physico-chemical impact thereof.

The possible position, design and size of a sparger in relation to a stirrer is evaluated and discussed in Sardeing et al.: "Gas-liquid mass transfer", Chemical Engineering Research and Design, Elsevier, Amsterdam, NL, Vol. 82, No. 9, 2004, pp. 1161-1168; Birch et al.: "The Influence of Sparger Design and Location on Gas Dispersion in Stirred Vessels", Chemical Engineering Research and Design, Elsevier, Amsterdam, NL, Vol. 75, No. 5, 1997, pp. 487-496 and Rewatkar V. B. et al.: "Role of sparger design on gas dispersion in mechanically agitated gas-liquid contactors", Canadian Journal of Chemical Engineering, 1993, Vol. 71, No. 2, pp. 278-291. In order to evaluate the effects only single spargers are used. The presence of two spargers in a reactor at the same time and the distance between them is not relevant and not mentioned.

It is therefore an object of the present invention to overcome the deficiencies of prior art and to provide a modified bioreactor or fermenter which allows to manage the carbon dioxide concentration independently from the oxygen concentration within an aerated stirred bioreactor or fermenter on industrial scale.

Furthermore, it is a further object to provide a method to control cell culturing or fermentation processes by an independent management of carbon dioxide concentration and oxygen concentration within an aerated stirred bioreactor or fermenter on industrial scale.

SUMMARY OF THE INVENTION

Surprisingly, it was found that the disadvantages known from prior art may be overcome, particularly an independent management of $O_2$- and $CO_2$-concentration in industrial scale aerated stirred bioreactors or fermenters may be achieved when a second gas supply (or optionally more gas supplies) is (are) arranged in a predefined distance from the first gas supply within the bioreactor.

Therefore, in order to overcome the above mentioned disadvantages, a modified and thereby improved bioreactor or fermenter for the culturing of cells or microorganisms in suspension in a liquid medium in industrial scale is provided. A bioreactor or fermenter 100 for the culturing of cells or microorganisms in suspension in a liquid medium in industrial scale according to the present disclosure comprises a vessel 102 containing the culture in a liquid medium having a determined filling height;

a stirrer 120 provided in the vessel to stir the liquid medium;

a first sparger 150 arranged in the bottom portion 105 of the vessel 102 provided to supply gas bubbles 10, 10.1, 10.2, 10.3 continuously to the liquid medium, the gas being selected from air and/or oxygen gas; and a second sparger 160 arranged in the vessel 102 and provided above the first sparger 150 to supply additional air bubbles and/or additional oxygen gas bubbles 20, 20.1, 20.2, 20.3 continuously to the liquid medium, whereby
the second sparger 160 is located at a position in the bioreactor or fermenter 100 above the first sparger 150 in a distance η whereby η is selected to be in the range from at least about 0.4 m above the first sparger 150 to at most about 0.5 m below the filling height of the bioreactor or fermenter 100 or about 0.4 m above the first sparger to about ⅔ of the filling height of the bioreactor or fermenter 100 or about 0.4 m above the first sparger to about ½ of the filling height of the bioreactor or fermenter 100 or about 0.4 m above the first sparger to about 3.0 m above the first sparger or about 0.4 m to about 2.5 m or about 0.4 m to about 2.0 m or about 0.4 m to about 1.5 m or about 0.4 to about 1.0 m or about 0.45 to about 0.90 m or about 0.5 to about 0.80 m or about 0.55 to about 0.70 m or at about 0.6 m.

Therefore, in order to enhance the mass transfer performance for $CO_2$, whereby at the same time the mass transfer performance for $O_2$ is not adversely affected, according to the invention an additional second gas sparger is provided within the bioreactor or fermenter at a higher position than the first sparger in a distance η, to achieve a much shorter residence time of the additional gas supplied compared to the gas provided from the submerse or first sparger. Due to the short residence time of the gas injected by the second sparger, a smaller amount of oxygen is transferred to the liquid phase whereas an increased amount of $CO_2$ can be stripped.

According to an embodiment the second sparger may be a side-sparger, i.e. a sparger which provides the additional gas bubbles nearby the sidewall.

BRIEF DESCRIPTION OF THE DRAWINGS

Embodiments of the prior art and of the present invention will be described by way of example with reference to the accompanying figures, which are schematic and are not intended to be drawn to scale so that no assumption of precise geometric values can be made regarding the original size. The figures of the present disclosure are incorporated in and constitute a part of the specification, also illustrating embodiments of the invention without limitation to the specific embodiments described. The drawings together with the general description and detailed description serve to explain the principles of the present disclosure. The same features are denoted by the same reference signs throughout the figures. In the figures.

Figure 1:
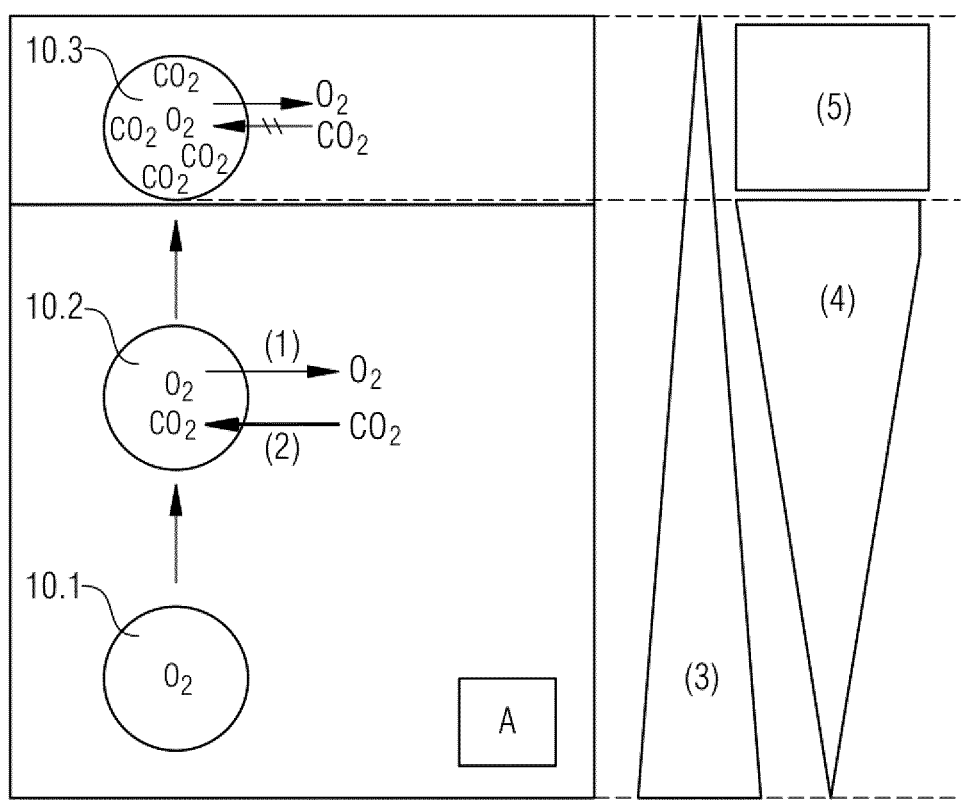
FIG. 1 shows a schematic illustration of the processes and reactions with regard to the distribution of $O_2$ and $CO_2$ which take place in a gas bubble in a bioreactor or fermenter.

The detailed legends to some figures are provided at the end of the present description.

DETAILED DESCRIPTION OF THE INVENTION

Terms not specifically defined herein should be given the meanings that would be given to them by a person skilled in the art in light of the disclosure and the context.

A "bioreactor" is a device or apparatus in which living organisms and especially bacteria and eukaryotic cells grow and/or synthesize useful substances thereby consuming the nutrients from the cultivation medium and—in case of aerobic cells or microorganims—$O_2$ which is provided by technical means like spargers. In the present disclosure the bioreactor is an industrial scale bioreactor. A bioreactor may consist of or comprise a biocompatible vessel in which a chemical or biochemical method is carried out which involves organisms and/or biochemically active substances derived from such organisms. A bioreactor uses additional equipment, for example stirrers, baffles, one or more spargers (as e.g. subject to the invention) and/or ports, which specifically allows for the cultivation and propagation of the cells. Commonly the bioreactor is in the form of a cylindrical tube, having two end parts, the end parts forming the top and the bottom of the bioreactor. The bioreactor ranges in size from litres to cubic metres and is often made of stainless steel. The bioreactor according to the present disclosure is used in large-scale production.

The cultivated cells, esp. eukaryotic cells like chinese hamster ovary (CHO) or yeast cells are for example used to produce antibodies such as monoclonal antibodies and/or recombinant proteins such as recombinant proteins for therapeutic use. Alternatively, the cells may produce, for example, peptides, amino acids, fatty acids or other useful biochemical intermediates or metabolites or any other useful substances.

A "fermenter" is a device or apparatus in which microorganisms synthesize useful substances whereby suitable conditions for the growth of microorganisms are maintained. The above-mentioned particulars for a bioreactor apply mutatis mutandis. The fermenter of the present disclosure is used in large-scale fermentation. Known commercial products of large-scale fermenters are, e.g., antibiotics, antibodies, hormones or enzymes synthesized by such cells or microorganisms.

The produced microorganisms are useful for different purposes, such as waste water treatment, in the food industry for the production of foodstuff, in the biotechnological sector for the manufacturing of drugs such as antibiotics or insulin, in the pest control, or in the biodegradation of waste, pollutants e.g. oil contamination.

In the present disclosure the expressions "industrial scale" or "large-scale" are used interchangeably and synonymously and relate to a product which is obtained in a large production amount whereby there is often a cost advantage with costs per unit of output decreasing with increasing scale. A large manufacturing unit is to be expected to have a lower cost per unit of output than a smaller unit, all other factors being equal. An industrial scale may be understood in connection with the cultivation of cells to have a volume of the bioreactor used which is equal or greater than about 2,000 L. An industrial scale may be understood in connection with the cultivation of microorganisms to have a volume of the fermenter used which is equal or greater than about 1,000 L. According to a further embodiment the volume of the bioreactor or fermenter used in industrial scale may be equal or greater than 6,000, 8,000, 10,000, 12,000, 15,000 L or even more.

A "stirrer" is an object or mechanical device used for stirring such as a magnetic stirrer. Any kind of stirrer commonly used in the culturing of cells or microorganisms may be used. Stirrers which may be used are, for example, impellers, Rushton-Turbine, stirring paddles, blade stirrers such as pitched blade stirrers and the like.

A "sparger" is a gas supply or feed device used in a bioreactor or fermenter which provides oxygen and/or air bubbles into the liquid phase and which is present in the liquid phase wherein cells or microorganisms are cultivated. A bioreactor or fermenter according to prior art has only one sparger which is usually positioned on or close to the bottom part thereof. In the present disclosure this sparger is also designated as "first sparger" or "submerse sparger", both expressions are used interchangeably and synonymously.

According to the present disclosure it has been found that providing a further sparger, namely a second sparger, which is positioned above the first sparger in a predefined distance η and supplies additional air bubbles and/or additional oxygen gas bubbles continuously to the liquid medium has a variety of advantages for the culturing process which will be obvious for the skilled person from the foregoing and following description.

In the following the processes and reactions which take place in a bioreactor or fermenter according to the present disclosure are described in greater detail.

In a bioreactor or fermenter where only one gas supply device is present—usually in the lower part or bottom of the bioreactor or fermenter—the bubbles which enter into the liquid phase have the capacity to take up $CO_2$ from the cell culture medium, but such capacity is more and more lost in the course of the ascending of the bubbles. In the upper or top part of the bioreactor or fermenter no more uptake of solved $CO_2$ of the bubbles from the liquid phase takes place, depending on the height as explained above. Thus, the $CO_2$ content is increasing from the bottom to the top of the bioreactor or fermenter thereby leading to a gradient of $CO_2$ within the liquid phase.

The $CO_2$ gradient normally present in the liquid phase of a bioreactor or fermenter and the disadvantages associated with such an inhomogeneous distribution of $CO_2$ may be overcome by the present disclosure according to which a second sparger is provided above a first sparger in a distance η spaced apart from the first sparger in the liquid phase of a bioreactor or fermenter in large-scale. The second sparger is provided to counteract the establishing $CO_2$ saturation of bubbles which are no longer able to absorb $CO_2$. The second sparger adds new gas bubbles into the liquid phase so that the processes of passing over $O_2$ and $CO_2$ may proceed again additionally above the first sparger.

Figure 5:
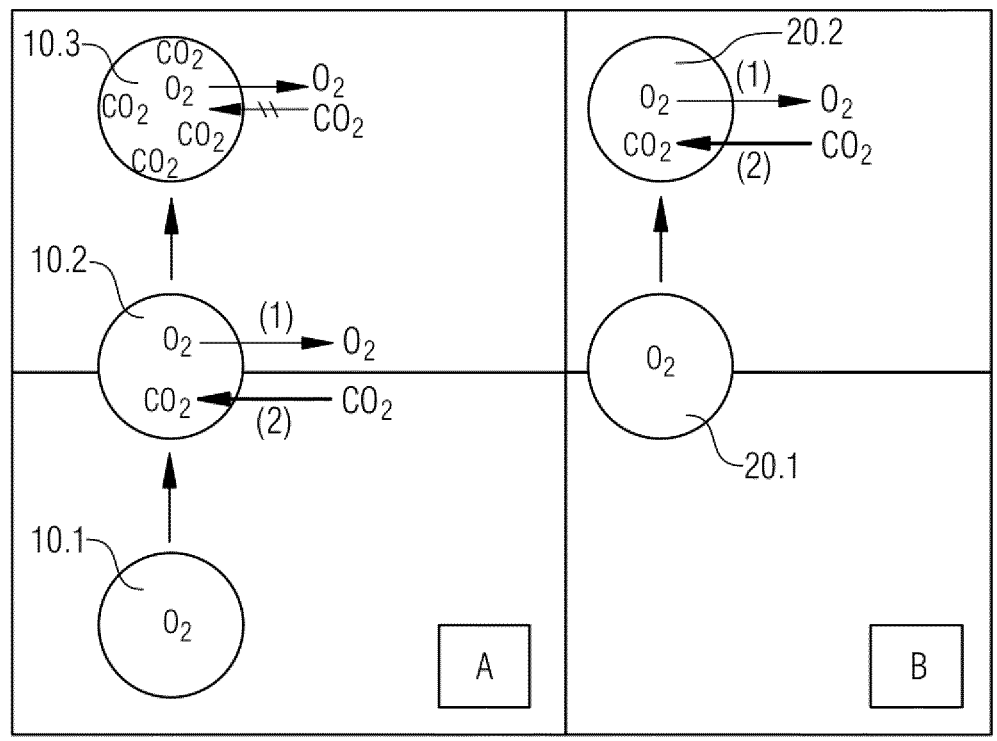
FIG. 5 shows a schematic illustration of the processes and reactions with regard to the distribution of $O_2$ and $CO_2$ which take place in a gas bubble 10 in a bioreactor or fermenter without an additional injection of gas (section A) and with an additional injection of gas (section B; bubble 20) according to an exemplary embodiment of the present disclosure.

By way of illustration the processes and reactions in question which take place in the liquid phase in a bioreactor or fermenter in large-scale are schematically shown in FIG. 5. FIG. 5, on the left section A, exemplifies the distribution of dissolved $CO_2$ in a schematic bioreactor or fermenter having only one gas supply device or sparger near to a stirrer (not shown). The sparger is located at or nearby the bottom of the bioreactor or fermenter. The standard gassing with only one sparger clearly results in a $CO_2$ gradient. After a specific height has been reached the bubble 10.2 is saturated with $CO_2$. Therefore, in the lower portion of FIG. 5 (section A) the stripping performance of $CO_2$ is well whereas in the upper portion the $CO_2$-stripping is poor and inacceptable.

FIG. 5, the right section B, illustrates the distribution of dissolved $CO_2$ in a schematic bioreactor or fermenter in large-scale as a result of an additional second gas supply device or second sparger provided above a first sparger. As may be derived from FIG. 5, section B, the second sparger provides the bubble 20.1 which begins its rising up to the surface in the liquid medium. As shown in bubble 20.2 $O_2$ gas passes over from the bubble 20.2 into the liquid phase (reaction (1)) and $CO_2$ gas passes over from the liquid phase into the bubble 20.2 (reaction (2)), whereby the rate of reaction (2) is much faster compared with the rate of reaction (1) (which is illustrated in FIG. 5 with the different thickness of the arrows) due to the different Henry's constants. Therefore, the stripping of $CO_2$ in the middle and the upper part of the liquid phase in section B is similar to the $CO_2$-stripping in the lower part of the liquid phase as shown on the left side of FIG. 5, in section A. Therefore, a $CO_2$ gradient over the whole ascending height in the liquid medium is avoided. The cells or microorganisms present in the bioreactor or fermenter would experience a more consistent milieu and would be subject to a much lesser extent of fluctuations of the liquid medium which could reflect in a metabolically reaction of the cells or microorganisms.

The second sparger is provided above the first sparger in order to shorten the absolute ascending height of a bubble in such a manner to avoid that the bubble may be saturated with $CO_2$ during its rise through the liquid phase. In addition, the residence time of the bubble originating from the second sparger within the liquid phase is decreased, the bubble ascends relatively fast to the liquid surface because it is not dispersed by an agitator. Therefore, the $CO_2$-stripping performance is also well in the upper portion of the bioreactor or fermenter.

According to a further embodiment a third sparger and also further spargers may be present above the second sparger etc. so that 3 spargers, 4 spargers or more are present at the same time in the bioreactor or fermenter. The above explanations for the second sparger apply for the third, fourth, fifth and further spargers accordingly.

Consequently, the large-scale bioreactor or fermenter is subdivided in different sub-compartments in each of which a sparger is arranged in order to have a direct influence on the $CO_2$ distribution in the liquid phase. This kind of "separation" of the large-scale bioreactor or fermenter in smaller units opens up an improved comparability and therefore improved predictability of the culturing in industrial scale vis-à-vis a laboratory scale and the reverse, advantageously with elevated metabolic rates, increased viability and/or increased productivity.

Providing a second sparger or optional a third and further spargers within the bioreactor or fermenter run in large production scale effects a harmonisation of the physico-chemical environmental conditions of the cells or microorganisms to be cultivated notwithstanding the large volume used. Therefore, the present concept is an approach to adapt the industrial scale to a laboratory scale in that the $CO_2$ distribution is more homogeneously over the whole liquid phase.

In addition, the dissolved $CO_2$ concentration in the liquid phase may be decreased to a suitable concentration or level due to the presence of a second sparger or optional third and further spargers. Keeping in mind that the $CO_2$ concentration affects cell-culture performance particularly at higher concentrations, whereby high $CO_2$ concentrations inhibit the growing of aerobic cells (cf. David R. Gray et al., $CO_2$ in large-scale and high-density CHO cell perfusion culture, Cytotechnology 1996, 22, 65-78), high $CO_2$ concentrations have to be avoided in a cell culturing medium per se. A second sparger and an additional third or additional further spargers assist to prevent the occurrence of such undesired high $CO_2$ contents in the liquid phase.

Furthermore, the additional second and also third and further spargers which supply additional air bubbles and/or additional oxygen gas bubbles continuously to the liquid medium result also in a $O_2$ distribution being more homogeneous over the whole liquid phase.

Therefore, according to a further embodiment (a) further sparger(s) provided above the first, second and third spargers may be present.

It has been found that the position of the second and also further spargers may have a positive impact on the performance and efficiency of the culturing in view of the management of the $O_2$- and $CO_2$-concentration in the liquid phase.

Presuming that a first sparger is located at or nearby the bottom or lower part of a bioreactor or fermenter, the second sparger is always located above the first sparger, for example in the middle or upper part of the bioreactor or fermenter. In order to further verify the position of the second sparger, in essence, there exist two main directions to vary the location of a second sparger within a bioreactor or fermenter in large scale. One main direction is the vertical direction, namely, to vary the position of a sparger from the bottom to the top of the bioreactor or fermenter. That is the second sparger may be positioned for example closer to the bottom or closer to the top of the bioreactor or fermenter or at any distance therebetween. In this regard the filling height of the bioreactor or fermenter has to be observed and not the absolute volume thereof because the gas bubbles are to be provided within the liquid phase present.

According to an embodiment of the invention the bioreactor or fermenter comprises a filling height in the range from about 8 to about 20 m or about 9 to about 15 m or about 9.5 to about 12 m or about 10 m.

A second main direction which may be taken into account is the horizontal direction, namely the location of the sparger between the side wall and the central axis of the bioreactor or fermenter. The central axis is the imaginary line within a bioreactor or fermenter which is presumed to have a cylindrical geometry and for which the spacing to the surrounding sidewall is everywhere equal or almost everywhere equal. That is the second sparger may be positioned for example closer to the sidewall or closer to the central axis of the bioreactor or fermenter or at any distance therebetween.

According to a further embodiment consecutive spargers may be accurately positioned one above the other in vertical direction. According to another embodiment consecutive spargers may be also located laterally shifted to each other with regard to the vertical direction.

Therefore, according to the present invention the second sparger is located at a position within the vessel of the bioreactor or fermenter in a distance $\eta$ from the first sparger. The distance $\eta$ is to be understood as a vertical distance, for example along the sidewall of the bioreactor or fermenter, so that the second sparger is located in a distance $\eta$ above the first sparger. The distance $\eta$ is selected to be in the range from at least about 0.4 m above the first sparger to at most about 0.5 m below the filling height of the bioreactor or fermenter or
  about 0.4 m above the first sparger to about ⅔ of the filling height of the bioreactor or fermenter or
  about 0.4 m above the first sparger to about ½ of the filling height of the bioreactor or fermenter or
  about 0.4 m to about 3.0 m, or about 0.4 m to about 2.5 m or about 0.4 m to about 2.0 m or about 0.4 m to about 1.5 m or
  about 0.4 to about 1.0 m or about 0.45 to about 0.90 m or about 0.5 to about 0.80 m or about 0.55 to about 0.70 m or at about 0.6 m, above the first sparger, respectively.

Therefore, the distance $\eta$ between the first and the second sparger has a lower limit of about 0.4 m above the first sparger and an upper limit of about 0.5 m below the filling height of the bioreactor or fermenter. The expression "filling height" which is used synonymously to the 'liquid height' is to be understood to mean the filling level of the liquid being present in the bioreactor or fermenter at the starting of the culturing process which is further defined by the surface of the liquid or the nominal volume of the liquid present. Thus, 0.5 m below the filling height of the bioreactor or fermenter is synonymous to 0.5 m below the surface of the liquid being present in the bioreactor or fermenter at the start of the culturing process.

If, for example, the total filling height is 10 m, 0.5 m below the filling height is 9.5 m. The distance $\eta$ is then selected in the range from about 0.4 m to about 9.5 m. The lower and upper limits of this range are considered to be critical values for the present invention.

The presence of the two spargers in the bioreactor per se increases the area in the liquid medium where $CO_2$-stripping will take place. If the second sparger is placed near the surface of the liquid, e.g. about 0.5 m below the filling height of the bioreactor or fermenter, it may strip the area downstream while the first sparger being placed near the bottom of the bioreactor may strip the area upstream of the liquid medium. In sum, the full filling height of the bioreactor or fermenter is subjected to a $CO_2$-stripping.

The distance $\eta$ may be selected to be in the range from about 0.4 m above the first sparger to about ⅔ of the filling height of the bioreactor or fermenter. The expression "about ⅔ of the filling height of the bioreactor or fermenter" shall be understood to mean the second sparger is located at a position where about ⅔ of the total filling height is achieved. If, for example, the total filling height is 12 m, ⅔ of the total filling height is 8.0 m. The distance $\eta$ is then selected in the range from about 0.4 m to about 8.0 m.

The distance $\eta$ may also be selected to be in the range from about 0.4 m above the first sparger to about ½ of the filling height of the bioreactor or fermenter. The expression "about ½ of the filling height of the bioreactor or fermenter" shall be understood to mean the second sparger is located at a position where about ½ of the total filling height or about 0.5-fold of the liquid volume is present. If, for example, the total filling height is 11 m, ½ of the total filling height is 5.5 m. The distance $\eta$ is then selected in the range from about 0.4 m to about 5.5 m.

The distance $\eta$ may also be selected to be in the range from about 0.4 m to about 3.0 m or about 0.4 m to about 2.5 m or about 0.4 m to about 2.0 m or about 0.4 m to about 1.5 m or about 0.4 to about 1.0 m or about 0.45 to about 0.90 m or about 0.5 to about 0.80 m or about 0.55 to about 0.70 m or at about 0.6 m. Therefore, distance $\eta$ may be selected to be about 3.0 m, about 2.9 m, about 2.8 m, about 2.7 m, about 2.6 m, about 2.5 m, about 2.4 m, about 2.3 m, about 2.2 m, about 2.1 m, about 2.0 m, about 1.9 m, about 1.8 m, about 1.7 m, about 1.6 m, about 1.5 m, about 1.4 m, about 1.3 m, about 1.2 m, about 1.1 m, about 1.0 m, about 0.95 m, about 0.90 m, about 0.85 m, about 0.80 m, about 0.75 m, about 0.70 m, about 0.65, about 0.6 m, about 0.55, about 0.45 and about 0.4 m, above the first sparger, respectively.

In further embodiments the distance $\eta$ may be selected to be in the range from at least about 0.6 m above the first sparger to at most about 0.5 m below the filling height of the bioreactor or fermenter or
  about 0.6 m above the first sparger to about ⅔ of the filling height of the bioreactor or fermenter or
  about 0.6 m t above the first sparger or about ½ of the filling height of the bioreactor or fermenter or
  about 0.6 m to about 3.0 m above the first sparger or about 0.6 m to about 2.5 m above the first sparger or about 0.6 m to about 2.0 m above the first sparger or about 0.6 m to about 1.5 m above the first sparger or
  about 0.6 m to about 1.0 m above the first sparger or about 0.6 m to about 0.90 m above the first sparger or about 0.6 m to about 0.80 m above the first sparger or about 0.6 m to about 0.70 m above the first sparger or at about 0.6 m above the first sparger.

The term "about" followed by a value shall be understood to mean the value±5% or the value±4% or the value±3% or the value±2% or the value±1%.

In order to determine the distance $\eta$ it is a matter of course that the position of the gas outlet opening(s) of the sparger(s), i.e. the opening(s) where the gas bubbles enter the liquid phase, are the key criterion. If several openings are present in one sparger a mean value may be used to determine the suitable distance.

The above mentioned ranges and values for the distance $\eta$ are the result of a variety of experiments, calculations as well as assessments performed according to which the second sparger is provided in the bioreactor or fermenter in a distance from or ascending height above the first sparger, at which the bubbles have reached or will soon reach the $CO_2$ gas phase saturation concentration.

The assessment of the $CO_2$ gas phase saturation concentration over the height of an industrial scale aerated stirred bioreactor or fermenter has been performed based on the following considerations:

According to our experiments (cf. FIGS. 2 to 4) the volumetric mass transfer coefficient for carbon dioxide $k_L a_{CO2}$ in an industrial scale aerated stirred bioreactor or fermenter of 12,000 L is about ten times lower than the volumetric mass transfer coefficient for carbon dioxide $k_L a_{CO2}$ in laboratory scale (2 L). In contrast, the amount of the volumetric oxygen mass transfer coefficient $k_L a_{O2}$ for both systems is comparable.

As known and opposed to the oxygen mass transfer, the mass transfer of carbon dioxide from the continuous liquid phase into the gas phase is already completed after a short period of time. In case the residence time of the gas phase in a system is longer than the period of time until the saturation of the gas bubbles occurs, these gas bubbles are no longer available for the $CO_2$ mass transfer. As a result, this effect arises only in reactors in industrial scale but not in laboratory scale.

For the assessment of the period of time after which the gas bubbles have been saturated with $CO_2$ in an industrial scale system (e.g. 12,000 L) during operation, wherein the gas bubbles do no longer contribute to the stripping of $CO_2$, the specific space boundary interface as well as the $CO_2$ mass transfer coefficient $k_L a_{CO2}$ has to be taken into account.

Therefore, at first, the assessment of the residence time distribution of the gas phase has been made as follows:

The gas phase residence time has been determined by the step response method ("Sprungantwortmethode") as explained in the experimental section in detail. The results in detail are given in the experimental section. The step function response method is based on the use of 2 different gases, one gas such as oxygen is used to saturate a liquid such as water and the other gas such as carbon dioxide or nitrogen gas is used to replace it and to drive it out of the liquid phase. The addition of gas is conducted from the bottom of the bioreactor or fermenter and the driven out gas is measured near the top of the reactor within the liquid phase. The skilled person is familiar with this method to measure the gas phase residence time.

Thus, using the step function response method, the gas phase residence time of a bioreactor or fermenter in laboratory scale (30 L) has been determined to be 5 s and the gas phase residence time for a bioreactor or fermenter in an industrial scale (12,000 L) has been found to be 21 s.

Then, according to further experimental measurements and assessments described in the experimental section the mass transfer coefficient of $CO_2$ has been identified in a laboratory scale bioreactor or fermenter (2 L) to be $4\pm0.68$ $h^{-1}$.

Under the assumption that the monodisperse distribution of the size of bubbles in a 12,000 L system is d=5 mm, the theoretical carbon dioxide profile in a single bubble may be calculated. The concentration profile of $CO_2$ in a bubble may be calculated under the assumption that the carbon dioxide mass transfer coefficient $k_L a_{CO2}=4\pm0.68$ $h^{-1}$ also applies for the industrial scale as follows:

$$c_{CO2}=c^*_{CO2}-\exp(k_L a A_{bubble}/V_{bubble}(c_{CO2}-c_{CO2})t+\ln(c^*_{CO2}))$$

From the experiment shown in example 6 (illustrated by FIG. 20) it could be deduced that a saturation of the gas bubbles of about 95% can be observed after about 3.5 s.

Based on the measured mean gas phase residence time in an industrial scale bioreactor or fermenter according to the same example, of about 21 s (FIG. 20) and the determined total distance travelled by the bubble of 3.6 m, the mean bubble rise velocity may be determined (velocity=distance/time) to be 0.17 m/s. As a result, after a height of about h=0.6 m (3.5 s×0.17 m/s) the gas phase is saturated with $CO_2$ and therefore no more stripping of $CO_2$ may be observed.

Since the above assessment, measurements and calculations include some evaluations and estimations the obtained result of 0.6 m is only an approximate value for the distance $\eta$ which is better represented by a range as from at least about 0.4 m above the first sparger to at most about 0.5 m below the filling height of the bioreactor or fermenter.

Further, it has been found in experiments that the presence of a second sparger provided in the distance $\eta$ has particular advantages for the culturing of cells or microorganisms in suspension in a liquid medium in industrial scale. It can be expected that the presence of a second sparger which is located above a first sparger in the distance $\eta$ which is selected in the above range will have a positive influence on the $CO_2$ stripping. The presence of the second sparger can be presumed to generate a decrease of the partial pressure of $CO_2$ in the culture (liquid medium) of the bioreactor or fermenter. That is, two bioreactors/fermenters are compared with each other, whereby both are operated under the same conditions with the same liquid medium and the same cells or microorganisms are cultured, respectively, the only difference between both bioreactors/fermenters is that in one bioreactor/fermenter one sparger is used (and thus reflects the state of the art) and in the other bioreactor/fermenter according to the invention two spargers located in a distance $\eta$ are used. Then, it can be expected that the partial pressure of $CO_2$ is decreasing by at least about 0.5%, or at least about 1% or at least about 2% up to about 20% in the bioreactor/fermenter having two spargers in comparison to the one with one sparger. The extent of the decrease of the partial pressure of $CO_2$ can be estimated based on experiments performed with one sparger (cf. Comparative Example 1 and FIG. 21) in connection with the evaluation measurements wherein two spargers have been used (cf. examples 2 to 6) which allows to draw conclusions about the content of $O_2$ and $CO_2$ present in the lower, middle and upper part of a bioreactor or fermenter.

Furthermore, if a second sparger is present as according to the invention a higher product titer and a higher product yield can be expected compared with a bioreactor or fermenter where only one sparger is used. The product titer or product yield produced can be presumed to be at least about 1% or at least about 5% or at least about 10% up to about 30% higher than in the same bioreactor or fermenter operated under the same conditions etc. where only one sparger is used. The extent of the product titer or yield can be estimated based on experiments performed with one sparger (cf. Comparative Example 1 and FIG. 21) in connection with the evaluation measurements wherein two spargers have been used (cf. examples 2 to 6) which allows to draw conclusions about the content of $O_2$ and $CO_2$ present in the lower, middle and upper part of a bioreactor or fermenter. It should be noted that also a small improvement in a process commercially used on a large scale represents a worthwhile technical problem to be solved. Given the total volume of representative large scale bioreactors of 10.000 L or more with millions of e.g. protein producing cells per ml, even small improvements in yield or other industrial characteristics mean a very relevant improvement in large-scale production and have to be regarded as significant.

Therefore, it has been found according to the invention that the selection of the distance $\eta$ in the described range or ranges has significant advantages and technical effects or benefits, particularly a decrease of the partial pressure of $CO_2$ in the culture (liquid medium) of the bioreactor and an increase of the product titer will occur, respectively.

The presence of the two spargers in the bioreactor or fermenter according to the invention increases the total area in the liquid medium where $CO_2$-stripping will take place. The second sparger may be placed in a distance $\eta$ whereby $\eta$ can be selected so that the areas where $CO_2$-stripping is performed by the first and the second sparger overlap to a certain extent. On one hand, it can be expected that an increasing degree of overlapping of the areas of the spargers will significantly improve the advantageous effects. On the other hand, if the two spargers are approaching too close, such as the distance $\eta$ being less than 0.4 m or less than 0.3 m or even smaller, the second sparger will most likely provide an increasingly smaller additional effect to the first sparger.

If the distance $\eta$ is selected to be in the range of from about 0.4 m above the first sparger to about ⅔ of the filling height of the bioreactor or fermenter it can be expected that the advantageous technical effects will become more prominent.

If the distance $\eta$ is selected to be in the range of from about 0.4 m above the first sparger to about ½ of the filling height of the bioreactor or fermenter it can be expected that the advantageous technical effects will become even more prominent.

If the distance $\eta$ is selected to be in the range of from about 0.4 m to about 3.0 m above the first sparger or more preferred from about 0.4 m to about 2.5 m above the first sparger or about 0.4 m to about 2.0 m above the first sparger or about 0.4 m to about 1.5 m above the first sparger or most preferred from about 0.4 to about 1.0 m above the first sparger or about 0.45 to about 0.90 m above the first sparger or about 0.5 to about 0.80 m above the first sparger or about 0.55 to about 0.70 m above the first sparger or at about 0.6 m above the first sparger it can be expected that the advantageous technical effects will become particularly strong.

Therefore, the distance $\eta$ between the first sparger and the second sparger and all further spargers, respectively, if present, is selected to be in the range or ranges as described above.

Therefore, if several spargers are present, in one embodiment the second sparger may be located in distance $\eta_{1,2}$ of 0.4 to 10 m above the first sparger; the third sparger may be located in distance $\eta_{2,3}$ of 0.4 to 10 m above the second sparger etc.

In order to distinguish between the different distances the distance $\eta$ between the first and second spargers is designated $\eta_{1,2}$, the distance between the second sparger and the third sparger is designated $\eta_{2,3}$ etc.

Therefore, the distance between two consecutive spargers, one arranged above the other, may be selected to be $\eta$.

The distance $\eta$ may be the same or different between all spargers which are present but it is always selected from the range as disclosed.

For the sake of better understanding the following example is presented:

A bioreactor or fermenter comprises a vessel and having a filling height of 10 m. The first sparger is present close to the bottom of the bioreactor or fermenter. The second sparger may be located in the bioreactor of fermenter in a distance $\eta$, also designated as $\eta_{1,2}$, between the first and the second sparger, whereby the distance $\eta_{1,2}$ is selected to be about 0.6 m spaced apart from the first sparger (determined as distance between the openings of both spargers, respectively, where the bubbles enter the liquid phase). A third sparger is located in a position with a distance $\eta_{2,3}$ between the second sparger and third sparger. In this example $\eta_{2,3}$ also amounts to 0.6 m. That is the second sparger is located 0.6 m above the position of the first sparger and the third sparger is located 0.6 m above the second sparger. Therefore, the third sparger is located in a distance 2×$\eta$ above the first sparger. Thus, $\eta_{1,2}$ and $\eta_{2,3}$ between the spargers are equally great. Further spargers present may have distances which may be $\eta_{3,4}$, $\eta_{4,5}$, $\eta_{5,6}$, . . . .

It is, however, not required that all distances have the same value but may be selected independently from each other from the above disclosed range. In other words $\eta_{1,2}$, $\eta_{2,3}$, $\eta_{3,4}$, $\eta_{4,5}$, $\eta_{5,6}$, . . . may be selected independently from each other and may be the same or different.

According to the second main direction the second sparger may be located closer to the sidewall or closer to the central axis of the bioreactor or fermenter so that the air bubbles and/or oxygen gas bubbles, provided from the second sparger, enter into the liquid phase closer to a sidewall or closer to the central axis of the bioreactor or fermenter.

According to another embodiment a second sparger may be also located in a position where the sparger has nearly the same distance to the side wall and the central axis of the bioreactor or fermenter at the same time.

Therefore, according to an embodiment the sparger(s) may be central spargers or side-spargers.

A "central sparger" has to be understood in the present disclosure in the sense that the central sparger is designed in such a manner that the air bubbles and/or oxygen gas bubbles from the sparger are provided into the liquid phase closer to a central axis than to the sidewall of the bioreactor or fermenter with regard to the horizontal direction.

A "side-sparger" has to be understood in the present disclosure as a sparger which is designed in such a manner that the air bubbles and/or oxygen gas bubbles are provided closer to a sidewall than to the central axis of the bioreactor or fermenter with regard to the horizontal direction.

According to an embodiment the first sparger may be a central sparger or a side-sparger.

According to another embodiment the first sparger may be a central sparger and the second sparger may be a central sparger.

According to another embodiment the first sparger may be a central sparger and the second sparger may be a side-sparger.

According to a further embodiment the first and second spargers may be side-spargers, respectively.

According to an embodiment the optional third sparger may be a central sparger or a side-sparger.

According to another embodiment the first sparger may be a central sparger and the second sparger may be a central sparger and the optional third sparger may be a central sparger.

According to another embodiment the first sparger may be a central sparger and the second sparger may be a side-sparger and the third sparger may be a side-sparger.

According to another embodiment the first sparger may be a central sparger and all other spargers may be side-spargers.

According to another embodiment the first sparger may be a side-sparger and all other spargers may be side-spargers.

It has been found in one embodiment that if the second sparger is a side sparger the advantageous technical effects as disclosed herein may be significantly increased.

According to another embodiment the second sparger may be constructed in such a manner that the openings thereof are directed downwards, i.e. the gas bubbles are provided in the direction to the bottom part of the bioreactor or fermenter.

The total number of spargers in a bioreactor or fermenter may be selected as required and depending from the filling height present. The spargers may be present over the whole filling height of the bioreactor or fermenter or only a part thereof. The number of spargers used depends from the type of cells or microorganisms selected, the dimensions of the bioreactor or fermenter, the conditions of culturing etc. The skilled person is readily able to select a suitable number of spargers for any culturing system used based on the explanations and statements as disclosed herein.

According to a further embodiment it has been found advantageous that the position of a stirrer present in the bioreactor or fermenter is taken into account in relation to the first and/or second and optional further spargers. Although the stirrer used is not limited in any way, any stirrer selected has a stirrer radius $r_s$ which is located around a central axis A through the bioreactor or fermenter. A number of experiments have shown that it is favourable when the first sparger is arranged at a distance from the central axis A of the bioreactor or fermenter such that the gas bubbles provided enter the liquid medium at a distance which is equal to or less than the stirrer radius $r_s$. In this connection it does not matter whether the first sparger is a central or a side sparger. In such a case the sparger provides the gas bubbles nearby the stirrer so that maximum turbulence is provided at the wing tips of a stirrer. Such a type of a high-energy mixing of liquid and gas is considered to be advantageous in the culturing of cells or microorganisms.

Further experimentation has shown that it is preferred that the second sparger and optional further spargers are fitted at a greater distance from the center than the stirrer radius $r_s$ so that the gas bubbles provided are outside or clearly outside of the stirrer movement. That is, the second sparger and optional further spargers are arranged at a distance from the central axis A such that the gas bubbles provided enter the liquid phase at a distance which is larger than the stirrer radius $r_s$. In this connection it does not matter whether the second sparger (and the further spargers) is (are) a central or a side sparger. In the present case the second sparger provides the gas bubbles spaced apart from the stirrer so that a turbulence is avoided which could deform or damage the gas bubbles provided. Therefore, a high-energy mixing of liquid and gas is considered to be disadvantageous for the effectivity of the second and optional further spargers because the beneficial technical effects such as the performance of the $CO_2$-stripping and the yield of the product could be negatively affected.

Figure 6A:
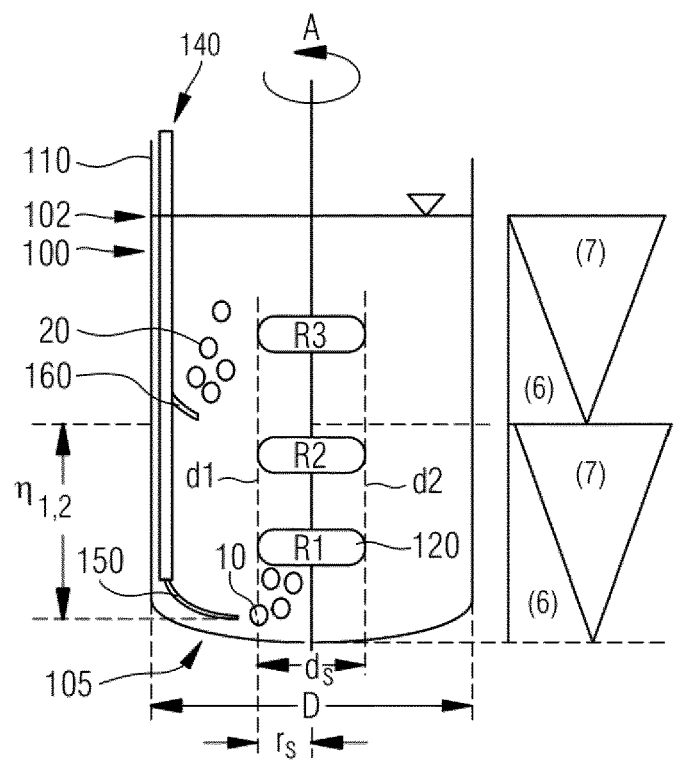
FIG. 6a illustrates the position of a first sparger 150 and a second sparger 160, respectively, in a bioreactor or fermenter according to an exemplary embodiment of the present disclosure.

In FIG. 6a the position of a first sparger 150 and a second sparger 160 in a vessel 102 of a bioreactor or fermenter 100 is exemplarily illustrated. The bioreactor or fermenter 100 has a bottom 105 and a sidewall 110 and has a diameter D. A gas supply tube 140 or several gas supply tubes (not shown) is(are) arranged nearby the sidewall 110 designed and installed in such a manner to form a first sparger 150 and a second sparger 160. The first sparger 150 is positioned at or nearby the bottom 105 of the bioreactor or fermenter 100 in the lower part thereof. In the embodiment shown the first sparger 150 is a central sparger, i.e. the gas bubbles enter the liquid phase closer to the central axis A than to the sidewall 110 with regard to a horizontal direction. However, it is also possible that the first sparger 150 may be a side-sparger as already explained.

The second sparger 160 is provided above the first sparger 150. In the embodiment shown the second sparger 160 is a side-sparger, i.e. the gas bubbles entering the liquid phase are located closer to the sidewall 110 of the bioreactor or fermenter 100 compared with the spacing to the central axis A with regard to a horizontal direction. However, it is also possible that the second sparger 160 may be a central sparger as already explained.

Figure 7:
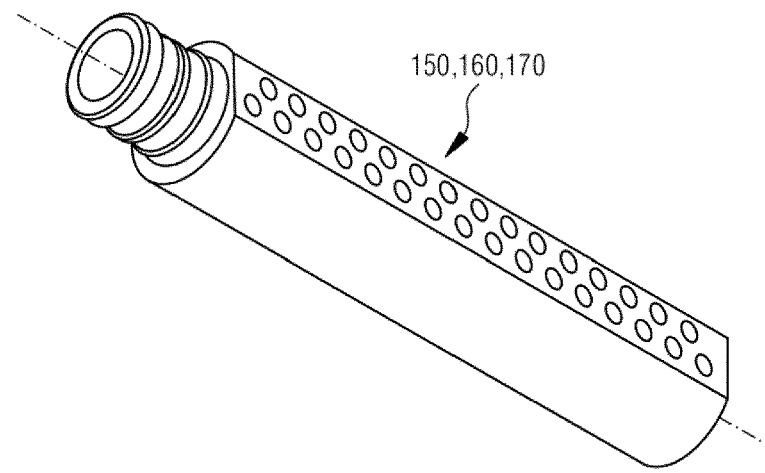
FIG. 7 shows a type of a sparger 150, 160, 170 according to an exemplary embodiment of the present disclosure.

FIG. 7 shows a schematic drawing of an exemplary type of sparger which may be used as side-spargers 150, 160, 170. As a matter of course also other useful sparger types are commercially available and may be used.

In FIG. 6a the second sparger 160 is located at a height or distance $\eta_{1,2}$ above the first sparger 150 in the bioreactor or fermenter 100. The distance $\eta_{1,2}$ is selected to be in the range of at least about 0.4 m above the first sparger 150 to at most about 0.5 m below the filling height of the bioreactor or fermenter 100 or about 0.4 m above the first sparger to about ⅔ of the filling height of the bioreactor or fermenter 100 or
about 0.4 m above the first sparger to about ½ of the filling height of the bioreactor or fermenter 100 or
about 0.4 m to about 3.0 m above the first sparger or about 0.4 m to about 2.5 m above the first sparger or about 0.4 m to about 2.0 m above the first sparger or about 0.4 m to about 1.5 m above the first sparger or about 0.4 to about 1.0 m above the first sparger or about 0.45 to about 0.90 m above the first sparger or about 0.5 to about 0.80 m above the first sparger or about 0.55 to about 0.70 m above the first sparger or at about 0.6 m above the first sparger. In FIG. 6a the second sparger 160 is located about ½ of the filling height of the bioreactor or fermenter 100. As shown in FIG. 6a the second sparger 160 makes "new" bubbles available which are able to absorb $CO_2$ from the liquid phase. As a consequence a better removal of solved $CO_2$ is possible. In the liquid phase an overall gradient of $CO_2$ is to a large degree avoided. The environmental conditions in an industrial scale bioreactor or fermenter are thus adjusted to be more similar to a small scale bioreactor or fermenter wherein the bubbles do not reach the $CO_2$ saturation concentration in their way upwards. Therefore, the stripping of growth inhibiting solved $CO_2$ is performed more efficiently from the culture suspension. Therefore, on the right side of FIG. 6a, the two arrows (6) from the broad part to the arrowhead, respectively, symbolize the absorption capacity for $CO_2$ from the liquid phase into the gas phase, which is decreasing. The arrows (7) in FIG. 6a symbolize the increasing saturation of the bubble with $CO_2$, from the arrowhead to the broad part, whereby $CO_2$ is passing over from the liquid phase into the gas phase which proceeds much faster than the delivery of $O_2$. Due to the presence of a further sparger the environmental milieu of the cells or microorganisms to be cultivated are adjusted more homogeneously.

Furthermore, referring to FIG. 6a and the exemplary embodiment shown a stirrer 120 having a stirrer radius $r_s$ is provided whereby the stirring or rotating axis corresponds to the central axis A. The stirrer 120 is composed of 3 stirrers R1, R2, and R3. The first stirrer R1 is located above a first sparger 150 situated at the bottom 105 or lower part of the bioreactor or fermenter 100. Furthermore, two additional stirrers R2 and R3 are provided in addition to the first stirrer R1, the additional stirrers R2 and R3 are located above and below the second sparger 160. According to another embodiment it is also possible to provide only a first stirrer R1 or to provide a first stirrer R1 and a second stirrer R2 at the same time. Also embodiments having more than 3 stirrers are possible.

In the embodiment shown in FIG. 6a a stirrer 120 has a stirrer radius $r_s$ located, in a symmetrical way, around a central axis A through the bioreactor or fermenter 100 resulting in a stirrer diameter $d_s$. The first sparger 150 is arranged at a distance from the central axis A (i.e. the opening of the first sparger is arranged at a distance) such that the gas bubbles provided enter the liquid phase at a distance which is equal or less than the stirrer diameter $d_s$ or stirrer radius $r_s$ as schematically illustrated with the dashed lines d1 and d2 in FIG. 6a. This finding is based on Klaas Van't Riet, Review of Measuring Methods and Results in Mass Transfer in Stirred Vessels Nonviscous Gas-Liquid, Ind. Eng. Chem. Process Des. Dev., Vol. 18, No. 3, 1979, p. 357-364, wherein it is stated that the sparger may not be fitted at a distance from the center larger than the stirrer radius. In case the first sparger is fitted at a distance from the central axis which is equal or less than the stirrer radius $r_s$ it is considered to be advantageous that maximum turbulence is provided at the wing tips of a stirrer. Further, a high-energy mixing of liquid and gas is considered to be advantageous in the culturing of cells or microorganisms. Therefore, this embodiment is considered to have advantages.

In FIG. 6a all stirrers R1, R2, and R3 have the same dimensions so that the stirrer radius $r_s$ and the diameter $d_s$ is the same for all three stirrers R1, R2, and R3 over the whole volume of the bioreactor or fermenter 100. Other embodiments are possible.

In the exemplary embodiment shown the stirrer has a stirrer radius $r_s$ and therefore a stirrer diameter $d_s$ located, in a symmetrical way, around a central axis A through the bioreactor or fermenter 100, whereby the second sparger 160 is arranged at a distance from the central axis A such that the bubbles provided enter the liquid phase at a distance which is larger than the stirrer radius $r_s$ or stirrer diameter $d_s$. In case the second and optional further sparger(s) provide the gas bubbles spaced apart from the stirrer, a turbulence is avoided which could deform or damage the gas bubbles provided. Therefore, a high-energy mixing of liquid and gas is considered to be less advantageous for the effectivity of the second and optional further spargers because the beneficial technical effects such as the performance of the $CO_2$-stripping and the yield of the product could be negatively affected.

When several stirrers are present the stirrer radius or diameter usually pertains to the stirrer which is located next to the sparger in question.

Figure 6B:
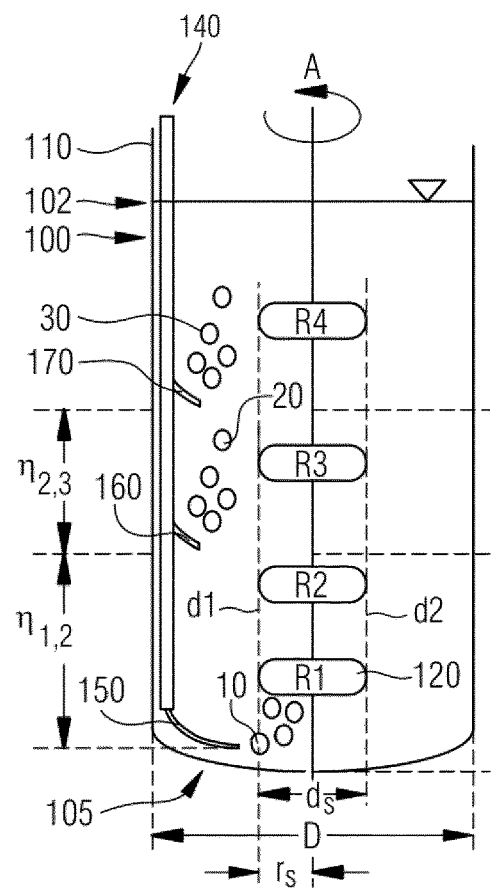
FIG. 6b illustrates the position of a first sparger 150, a second sparger 160, and a third sparger 170, respectively, in a bioreactor or fermenter according to an exemplary embodiment of the present disclosure.

Referring to FIG. 6b, besides a first sparger 150 and a second sparger 160, a third sparger 170 is provided whereby the third sparger 170 is located at the height or distance $\eta_{2,3}$ above the second sparger 160 in the bioreactor or fermenter 100. The distance $\eta_{2,3}$ may be selected from the range as herein defined above the second sparger 160. In FIG. 6b the second sparger 160 is located at about ⅓ of the filling height and the third sparger 170 is located at about ⅔ of the filling height of the bioreactor or fermenter 100.

It is expected that the presence of a second sparger according to the invention significantly decreases the partial pressure of $CO_2$ by at least about 0.5%, or at least about 1% or at least about 2% up to about 20% compared with a bioreactor/fermenter having only one sparger (reflecting the state of the art). Furthermore, it is expected that an increased product titer and an increased product yield of at least about 1% or at least about 5% or at least about 10% up to about 30% will be obtained compared with a bioreactor or fermenter where only one sparger is used. As said above even a small improvement in a process used in industrial scale as in the present invention represents a significant improvement with regard to e.g. possible duration of the overall process (extension of the fed-batch process by a few hours up to one, two or even three days), to the living cell density (viability of the cells) or to the resulting titer of the product.

Furthermore, it has been found that the provision of a second sparger and optionally further spargers, besides a first sparger, in a bioreactor or fermenter operated in large-scale already offers the possibility to establish an independent management of the $O_2$- and $CO_2$-concentration within the bioreactor or fermenter.

Therefore, it is provided a process to control and adjust the content of dissolved $CO_2$ and the content of dissolved $O_2$ in a liquid medium in a bioreactor or fermenter 100 for the culturing of cells or microorganisms in suspension in industrial scale comprising a vessel 102 containing the culture in a liquid medium;

stirring the liquid medium;

continuously supplying gas bubbles 10, 10.1, 10.2, 10.3 from a first sparger 150 arranged in the bottom portion 105 of the vessel 102 to the liquid medium, the gas being selected from air and/or oxygen gas;

continuously supplying gas bubbles 20, 20.1, 20.2, 20.3 from a second sparger 160 arranged in the vessel 102 to the liquid medium, the gas being selected from air and/or oxygen gas, whereby the second sparger 160 being arranged above the first sparger 150 and the second sparger 160 is a side-sparger;

selecting and adjusting a modified gas flow rate $q_{mod}(O_2)$ and selecting and adjusting a modified gas flow rate $q_{mod}(CO_2)$ which are both suitable for the culturing process, based on the gas flow rate $q_{sub}$ of the submerse or first sparger 150 and the gas flow rate $q_{side}$ of the side or second sparger 160, whereby the following equations apply:

$$q_{mod}(O_2) = q_{sub} + C_{O2} \times q_{side} \quad [1a]$$

and $$q_{mod}(CO_2) = q_{sub} + C_{CO2} \times q_{side} \quad [1b]$$

wherein $q_{sub}$ represents the gas flow rate of the submerse or first sparger 150;

$q_{side}$ represents the gas flow rate of the side or second sparger 160;

$C_{O2}$ represents an influence factor C of the volumetric oxygen mass transfer, whereby $C_{O2} = 0.15$; and $C_{CO2}$ represents an influence factor C of the volumetric carbon dioxide mass transfer, whereby $C_{CO2} = 0.6$.

The above process to control and adjust the content of dissolved $CO_2$ and the content of dissolved $O_2$ in a liquid medium in a bioreactor or fermenter for the culturing of cells or microorganisms in suspension in industrial scale will be explained in detail as follows:

It has been recognized that more precise predictions on the oxygen mass transfer performance as well as carbon dioxide mass transfer performance of an industrial scale aerated stirred bioreactor or fermenter can only be made based on detailed studies. Therefore, a number of experiments have been performed, wherein only a first sparger is present. Alternatively, the influence of an additional second sparger has been examined. It has been found that the oxygen mass transfer coefficient $k_L a_{O2}$ is directly proportional to the gas flow rate in case only one sparger is present. That is, when the gas flow rate is doubled the mass transfer coefficient is also almost doubled. That is one sparger may already provide sufficient oxygen mass transfer (characterised by $k_L a_{O2}$) to meet the oxygen demand of the culture.

Furthermore, it has been surprisingly found that the presence of an additional side-sparger and therefore an additional side aeration has almost no influence or only a small influence on the oxygen mass transfer coefficient $k_L a_{O2}$. Therefore, only the gas flow rate of the submerse or first sparger in a bioreactor or fermenter is of importance with regard to the mass transfer coefficient of oxygen $k_L a_{O2}$. As a result, the influence of the submerse aeration may be considered to be dominant for the oxygen mass transfer.

In addition, it has been observed, that a side-injection leads to a small increase of the mass transfer performance for oxygen whereas the mass transfer performance for carbon dioxide increases significantly. This finding substantiating another aspect of the invention was also completely unexpected. In fact, the side-sparger has a very strong influence on the mass transfer coefficient for carbon dioxide which increases much stronger with increasing side-injection. As a result, the influence of the side aeration may be considered to be dominant for the carbon dioxide mass transfer.

Since the side-injection of gas in an industrial scale aerated stirred bioreactor or fermenter has different influences on the mass transfer coefficient of oxygen and carbon dioxide it is possible to conduct an independent management of the oxygen concentration and the carbon dioxide concentration. The independent management may be based on the two principles, namely that the $CO_2$ mass transfer is almost constant if the total gas flow rate is constant and that the side-aeration has a different influence on the $CO_2$ mass transfer and the $O_2$ mass transfer.

In a number of evaluation measurements it has been found that the gas flow rate of the side-injection of gas cannot simply be added to the submerse gas flow rate. In fact, a "modified" gas flow rate must be assumed. Thus, a modified gas flow rate for carbon dioxide ($q_{mod}(CO_2)$) and a modified gas flow rate for oxygen ($q_{mod}(O_2)$) has to be taken into account, modified gas flow rates which are considered to be proportional to the mass transfer coefficients ($k_L a_{O2}$ or $k_L a_{CO2}$), respectively. Therefore, the gas flow rates may be used to have a direct influence on the $CO_2$ mass transfer and the $O_2$ mass transfer of the culturing process, respectively. The experiments (illustrated by FIGS. 10 and 11) have shown that the "modified" gas flow rates can be expressed by the following equations:

For oxygen:

$$q_{mod}(O_2) = q_{sub} + C_{O2} \times q_{side} \quad [1a]$$

wherein $C_{O2} = 0.15$.

For carbon dioxide:

$$q_{mod}(CO_2) = q_{sub} + C_{CO2} \times q_{side} \quad [1b]$$

wherein $C_{CO2} = 0.6$.

Said modified gas flow rates includes the submerse aeration $q_{sub}$ and the side aeration $q_{side}$ which is modified and weighted with an influence factor C. The higher the factor C is, the higher is the influence of the side-aeration on the mass transfer performance. The factor C can be calculated with the assumption that the mass transfer is linear proportional to the submerse gas flow rate. The detailed calculation of the influence factors C is explained and demonstrated in the examples section (Example 3).

The results show that a side-injection of gas leads to an increase of the mass transfer coefficient for oxygen by the influence factor $C_{O2}$ of 0.15 only whereas the mass transfer coefficient for carbon dioxide can be enhanced by the influence factor $C_{CO2}$ of 0.6. That is, a small increase of the mass transfer performance for oxygen is observed whereas the mass transfer performance for carbon dioxide increases significantly.

With this approach, the independent management of carbon dioxide and oxygen in industrial scale aerated stirred bioreactors or fermenters becomes possible. In other words, the influence factor for carbon dioxide ($k_L a_{CO2}$) is about four times higher in the side-injection of gas compared with the submerse aeration. Thus, the actual or modified gas flow rates of oxygen and carbon dioxide may be selected and adjusted in order to have the optimal conditions in the culturing system.

The following exemplary case shall clarify the above findings as follows:

The gas flow rate of the submerse or first sparger $q_{sub}$ is selected to have the following value: $q_{sub} = 120$ L/min.

The gas flow rate of the second sparger or side-sparger $q_{side}$ is selected to have the following value: $q_{side} = 60$ L/min.

Then, the modified gas flow rate for the oxygen mass transfer $q_{mod}(O_2)$ can be calculated according to equation [1a] as follows:

$$q_{mod}(O_2) = 120 \text{ L/min} + 0.15 \times 60 \text{ L/min} = 129 \text{ L/min}.$$

In addition, the modified gas flow rate for the carbon dioxide mass transfer $q_{mod}(CO_2)$ can be calculated according to equation [1b] as follows:

$$q_{mod}(CO_2) = 120 \text{ L/min} + 0.6 \times 60 \text{ L/min} = 156 \text{ L/min}.$$

Since $q_{mod}(O_2)$ represents the modified total gas flow rate which is considered to be proportional to the mass transfer coefficient $k_L a_{O2}$ the skilled person has a direct measure about the influence on the mass transfer of oxygen. Furthermore, $q_{mod}(CO_2)$ represents the modified total gas flow rate which is considered to be proportional to the mass transfer coefficient $k_L a_{CO2}$ and the skilled person has also a direct measure about the influence on the mass transfer of carbon dioxide. As a result, the above mentioned equations [1a] and [1b] allow to control and adjust the $O_2$ content as well as the $CO_2$ content based on the gas flow rates selected, respectively. The skilled person is readily able to select and adjust the suitable and desired $q_{mod}(O_2)$ as well as $q_{mod}(CO_2)$, which are optimal for the individual culturing processes and have a direct impact on the cell or microorganism culturing performance.

With this approach it is therefore possible to perform an independent management of carbon dioxide and oxygen in industrial scale aerated stirred bioreactors or fermenters if a second sparger in form of a side-sparger is provided. Furthermore, the skilled person has the possibility to adjust and select the gas flow rates of the first and second sparger such that $k_L a_{O2}$ and $k_L a_{CO2}$ may be controlled and adjusted for any specific process of culturing of cells or microorganisms.

Although the gas flow rate of the first sparger $q_{sub}$ may—according to one embodiment of the invention—be selected to be greater than the gas flow rate of the second sparger $q_{side}$, it is also possible to select that $q_{sub}$ is adjusted to be greater than $q_{side}$ ($q_{side} > q_{sub}$).

According to an embodiment and as already explained the distance $\eta_{1,2}$ between the first submerse sparger and the second side-sparger may be selected to be in the range as herein defined. It is therefore possible to arrange the second sparger in a height above the first sparger at which the bubbles have reached or will soon reach the $CO_2$ gas phase saturation concentration.

In a further embodiment a third sparger 170 and optional (a) further sparger(s) are provided in the bioreactor or fermenter 100 above the first sparger 150 and second sparger 160, the distance between two consecutive spargers 150, 160 and/or 160, 170, one arranged above the other, is selected to be η.

In addition to the first submerse sparger and the second side-sparger further spargers may be present in the bioreactor or fermenter as already described. The distances $\eta_{1,2}$, $\eta_{2,3}$, $\eta_{3,4}$ between the spargers, may be selected in the above range as already disclosed. The further spargers may be central spargers or side-spargers, decided individually for each sparger. Based on the above findings and explanations with regard to an independent management of $CO_2$ and $O_2$, according to an embodiment, the further spargers are all side-spargers.

Therefore, according to a further embodiment the first sparger is a central sparger or a side sparger and the second sparger and the optional third and further spargers are side-spargers. According to a further embodiment the first sparger is a central sparger and the second sparger and the optional third and further spargers are side-spargers.

Besides the varying of the gas flow rates of the spargers used there exist other parameters and conditions which may assist to improve the culturing performance of the cells or microorganisms like for example temperature, pH or concentrations of specific nutrients, stirrer type, stirrer velocity, sparger type, sparger size, sparger geometry . . . . The skilled person is familiar with these parameters and how to modify them.

The skilled person may select any sparger known from prior art to be used in the culturing process of cells or microorganisms. However, the type of sparger used may have an influence on the mass transfer performance of oxygen and carbon dioxide. The number and size of the openings present, the geometry and size of the sparger selected may play a part. It is presumed that larger gas bubbles as a result of larger openings, high bubble rise velocities and thus a short contact time between gas and media will allow a stronger removal of carbon dioxide with only weak supply of oxygen. Therefore, the skilled person is readily able to select suitable spargers based on his average skill in the art which are advantageous for each culturing process.

According to an embodiment the first, second and optional further spargers are static spargers selected from spargers with a pipe-geometry, for example tube type spargers such as open-tube spargers, sintering plates, perforated slabs, ring spargers, spider type spargers, disc type spargers, sheet type spargers, cup type spargers, and bushing type spargers.

In a further embodiment the first, second and optional further spargers are the same or different spargers.

According to a further embodiment the first, second and optional further spargers are spargers with a pipe-geometry, for example a tube type sparger such as an open-tube sparger.

In a further embodiment the first, second and optional further spargers are crescent tube type spargers, respectively.

According to a further embodiment the first, second and optional further spargers are crescent open-tube spargers, respectively.

A tube type sparger, particularly an open-tube sparger such as crescent open-tube sparger has the advantage of good cleaning capability and also offers the benefits of easier cleaning in place (CIP) and sterilisation in place (SIP).

Furthermore, the bioreactor or fermenter is not limited according to the present disclosure. Any aerated and stirred bioreactor or fermenter known may be used. Also bubble columns trickle bed reactors, loop reactors etc. may be used.

Also, the cells used are not limited according to the present disclosure. In an embodiment of the present disclosure the cells may be eukaryotic cells such as mammalian cells, particularly yeast (*S. cerevisiae, Pichia pastoris*), Chinese hamster ovary (CHO) cells, human cells (e.g. HEK 293) or insect cells. Also, other cells may be used.

The microorganisms are also not limited according to the present disclosure. In an embodiment of the present disclosure the microorganisms may be prokaryotic cells such as *E. coli* or *Bacillus subtilis*.

The present disclosure is also directed to a process for the culturing of cells or microorganisms in a bioreactor or fermenter as already described, wherein a second sparger is provided in the bioreactor or fermenter in a distance η as defined to promote the growth, viability, productivity and/or any other metabolic condition of the cells or microorganisms to be cultivated.

The present disclosure is also directed to a process for the culturing of cells or microorganisms in a bioreactor or fermenter as already described, wherein, besides a first and second sparger, (a) further sparger(s) (is)are provided in a distance η, respectively, as defined, in the bioreactor or fermenter to promote the growth, viability, productivity and/or any other metabolic condition of the cells or microorganisms to be cultivated.

The present disclosure is also directed to a second sparger provided in a bioreactor or fermenter for the culturing of cells or microorganisms as already described, wherein the second sparger is provided in the bioreactor or fermenter to promote the growth, viability, productivity and/or any other metabolic condition of the cells or microorganisms to be cultivated, whereby the second sparger is located at a position in the bioreactor or fermenter above the first sparger in a distance η whereby η is selected to be at least about 0.4 m above the first sparger to at most about 0.5 m below the filling height of the bioreactor or fermenter or about 0.4 m above the first sparger to about ⅔ of the filling height of the bioreactor or fermenter or about 0.4 m above the first sparger to about ½ of the filling height of the bioreactor or fermenter or about 0.4 m to about 3.0 m above the first sparger, or about 0.4 m to about 2.5 m or about 0.4 m to about 2.0 m or about 0.4 m to about 1.5 m or about 0.4 to about 1.0 m or about 0.45 to about 0.90 m or about 0.5 to about 0.80 m or about 0.55 to about 0.70 m or at about 0.6 m, above the first sparger, respectively.

The present disclosure is also directed to a second sparger and (a) further sparger(s) provided in a bioreactor or fermenter for the culturing of cells or microorganisms as already described, wherein the second sparger and (a) further sparger(s) are provided in the bioreactor or fermenter to promote the growth, viability, productivity and/or any other metabolic condition of the cells or microorganisms to be cultivated, whereby the second sparger is located at a position in the bioreactor or fermenter above the first sparger in a distance η whereby η is selected to be at least about 0.4 m above the first sparger to at most about 0.5 m below the filling height of the bioreactor or fermenter or about 0.4 m above the first sparger to about ⅔ of the filling height of the bioreactor or fermenter or about 0.4 m above the first sparger to about ½ of the filling height of the bioreactor or fermenter or
about 0.4 m to about 3.0 m above the first sparger, or about 0.4 m to about 2.5 m or about 0.4 m to about 2.0 m or about 0.4 m to about 1.5 m or about 0.4 to about 1.0 m or about 0.45 to about 0.90 m or about 0.5 to about 0.80 m or about 0.55 to about 0.70 m or at about 0.6 m, above the first sparger, respectively.

Consequently, an additional injection of gas at a higher position, such as an additional side-injection, for example, with large gas bubbles, high bubble rise velocities and thus a short contact time between gas and media leads to improved performance in the cell culturing process.

In addition, it is now, according to the invention possible to enhance the volumetric carbon dioxide mass transfer coefficient $k_L a_{CO2}$ for the large-scale system without affecting the oxygen mass transfer coefficient $k_L a_{O2}$ significantly. Thus, in a simplified form a first sparger is used to control and adjust the $O_2$ mass transfer and a second sparger in form of a side-sparger, and optional (a) further sparger(s) may be used to control and adjust the $CO_2$ mass transfer. In detail, the first sparger may be predominantly used to provide more $O_2$ to the culturing process whereas the second and optional (a) further sparger(s) may be predominantly used to lower the $CO_2$ content.

EXAMPLES

Example 1: Determination of $k_L a_{CO2}$

Figure 8:
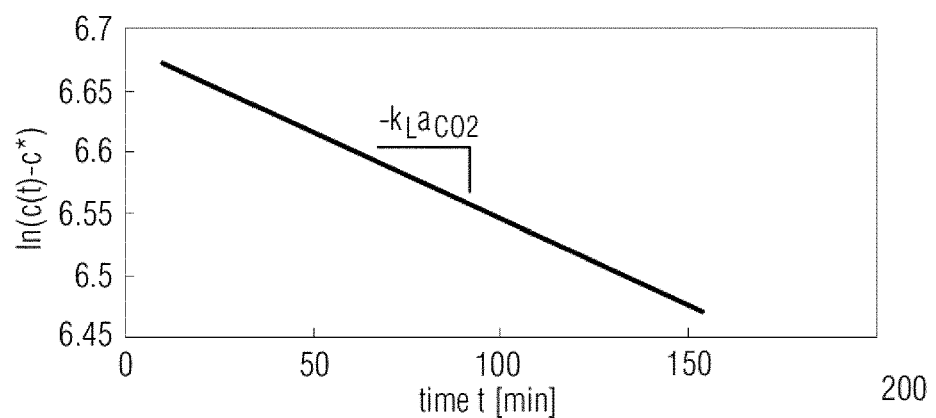
FIG. 8 is explained in the example section (Example 1) and shows an illustrative evaluation of the $k_L a_{CO2}$ value from a saturation of $c_{CO2}=14\%$ to $c_{CO2}=6\%$ according to an exemplary embodiment of the present disclosure.

For the determination of the volumetric mass transfer coefficient $k_L a_{CO2}$, the dynamic method is used. In the used method a bioreactor will be gassed with carbon dioxide until a saturation of 15% is reached. Subsequently, the desired stirrer frequency n and the desired rate of gassing q are set and the decrease of the concentration of carbon dioxide is being recorded. The plot of the recorded carbon dioxide levels against the corresponding time t is following equation [2] and can be described according to $$\frac{dc_{CO_2}}{dt} = k_L a_{CO_2}(c_{CO_2} - c^*) \quad [2]$$

with the volumetric mass transfer coefficient $k_L a_{CO2}$ and the saturation concentration c*. The equation can be transformed into a logarithmic expression as follows:

$$\frac{\ln(c^*_{CO_2} - c'_{CO_2})}{\ln(c^*_{CO_2} - c''_{CO_2})} = -k_L a_{CO_2}(t'' - t') \quad [3]$$

with the concentration $c'_{CO2}$ at the time t' and the concentration $c''_{CO2}$ at the time t". Equation [3] provides the value of $k_L a_{CO2}$ as the slope of the logarithmic function of the carbon dioxide plot. An exemplary evaluation can be found in FIG. 8. Referring to FIG. 8 the evaluation of the $k_L a_{CO2}$ value was done from a concentration of $c_{CO2}$=14% to $c_{CO2}$=6%. Therefore, the $k_L a_{CO2}$ is shown to be a negative value because a decrease of the $CO_2$ takes place. As a result, the $k_L a$ values are derived from the slopes of the logarithmic representation of the curves determined.

Example 2: First Evaluation Measurements

Figure 9:
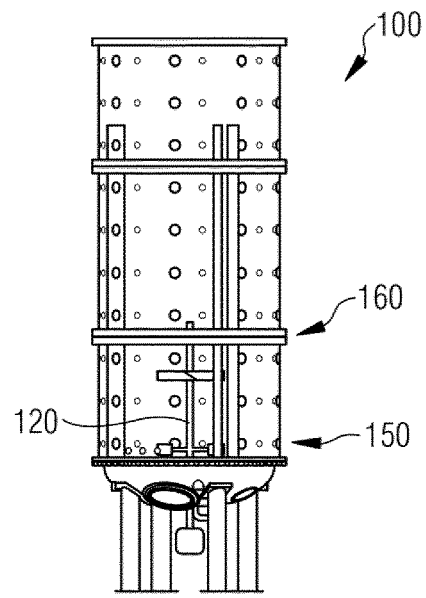
FIG. 9 is explained in the example section (Example 2) and shows a technical drawing of a vertical sectional schematic view of a bioreactor in industrial scale and the mounting position of an additional second sparger (160) according to an exemplary embodiment of the present disclosure.

In order to examine the oxygen mass transfer performance of an industrial scale aerated stirred bioreactor or fermenter a second sparger in form of a side-sparger has been designed and installed in a reactor. The measurements have been performed in a 15 kL bioreactor, filled with a volume of about 12 kL (see Table 1 below) of 0.9% (w/v) $NaCl/H_2O$. The technical drawing of the 15 kL bioreactor used and the mounting position of the additional side-sparger are shown in FIG. 9. In these measurements the additional side-sparger 160 is mounted at a position where the filling height represents one half of the reactor volume. $V_{Fill}$ represents the filling volume of the vessel of the bioreactor 100. That is, the side-sparger 160 is located at a position which represents 0.5-fold of the filling volume (% $V_{Fill}$) which in the present case is about ½ of the filling height of the bioreactor or fermenter because the form of the bioreactor or fermenter is of a cylindrical shape.

The submerse or first sparger used in these measurements (not shown) is a side-sparger in form of an tube type sparger having 31×2 mm drills, i.e. 31 openings, each opening has a diameter of 2 mm.

The second sparger used in these measurements is also a side-sparger in form of a tube type sparger having 15×3 mm drills i.e. 15 openings, each opening has a diameter of 3 mm.

The gas used in the submersed sparger (first sparger) as well as the side-sparger (second sparger) is air.

The first evaluation measurements have been performed to measure the mass transfer rate for oxygen in dependency of the gas flow rate for a stirrer frequency of n=60 rpm. A detailed overview of the investigated operation conditions and gassing strategies is given in Table 1.

TABLE 1 mass transfer rate for oxygen in dependency of the gas flow rate

| Setup | Volume $V_{Fill}$ [m$^3$] | Temperature θ [° C.] | Stirrer frequency n [rpm] | Total gas flow $q_{total, air}$ [L min$^{-1}$] | Submerse sparger gas flow $q_{sub, air}$ [L min$^{-1}$] | Side-sparger gas flow $q_{side, air}$ [L min$^{-1}$] |
|---|---|---|---|---|---|---|
| 1 | 12.5 | 37 | 60 | 120 | 120 | 0 |
| 2 | 12.5 | 37 | 60 | 120 | 100 | 20 |
| 3 | 12.5 | 37 | 60 | 140 | 120 | 20 |
| 4 | 12.5 | 37 | 60 | 180 | 120 | 60 |

Thus, in the measurements 1 to 4 the gas flow rates have been varied while the stirrer rate has been maintained constant.

In measurement 1 the gas flow rate of the submerse sparger or first sparger has been set to be 120 L/min. The side-sparger or second sparger does not provide air to the liquid medium, i.e. the gas flow rate of the second sparger is 0 L/min. The overall or total gas flow rate ($q_{total}$) in measurement 1 is therefore:

$q_{sub}+q_{side}$=120 mL/min+0 mL/min=120 mL/min.

In measurement 2 the gas flow rate of the submerse sparger or first sparger has been set to be 100 L/min; the gas flow rate of the side-sparger or second sparger has been set to be 20 L/min and the total gas flow rate is then 120 L/min.

In measurement 3 the gas flow rate of the submerse sparger or first sparger has been set to be 120 L/min; the gas flow rate of the side-sparger or second sparger has been set to be 20 L/min and the total the gas flow rate is then 140 L/min.

In measurement 4 the gas flow rate of the submerse sparger or first sparger has been set to be 120 L/min; the gas flow rate of the side-sparger or second sparger has been set to be 60 L/min and the total the gas flow rate is then 180 L/min.

Measurement 1, wherein no side gassing occurs, has been taken as a standard and the volumetric mass transfer coefficient $k_L a_{O2}$ of the measurements 2 to 4 has been determined in relation to this standard measurement. The volumetric mass transfer coefficient $k_L a_{O2}$ represents a direct measure for the mass transfer rate for oxygen.

In additional measurements it has been found that the mass transfer coefficient $k_L a_{O2}$ is directly proportional to the gas flow rate. When the gas flow rate is doubled the mass transfer coefficient is also almost doubled. This finding is confirmed in measurement 2 wherein the gas flow rate of the submerse sparger has been decreased from 120 L/min to 100 L/min. Although the total gas flow rate is kept at a constant level of 120 l/min in measurement 1 and measurement 2, respectively, the mass transfer coefficient $k_L a_{O2}$ is decreased to a value of −18% in measurement 2 compared with measurement 1. The side-sparger having a gas flow rate of 20 L/min has practically no effects on the mass transfer coefficient $k_L a_{O2}$. Therefore, only the gas flow rate of the submerse sparger (first sparger) plays a role for $k_L a_{O2}$. The influence of the submerse aeration is therefore considered to be dominant for the oxygen mass transfer.

In fact, in measurements 1 to 4 the mass transfer coefficients are not significantly influenced by the additional side-injection of gas. It is therefore confirmed that the side-aeration has almost no influence or only a small influence on the oxygen mass transfer coefficient $k_L a_{O2}$.

Figure 10:
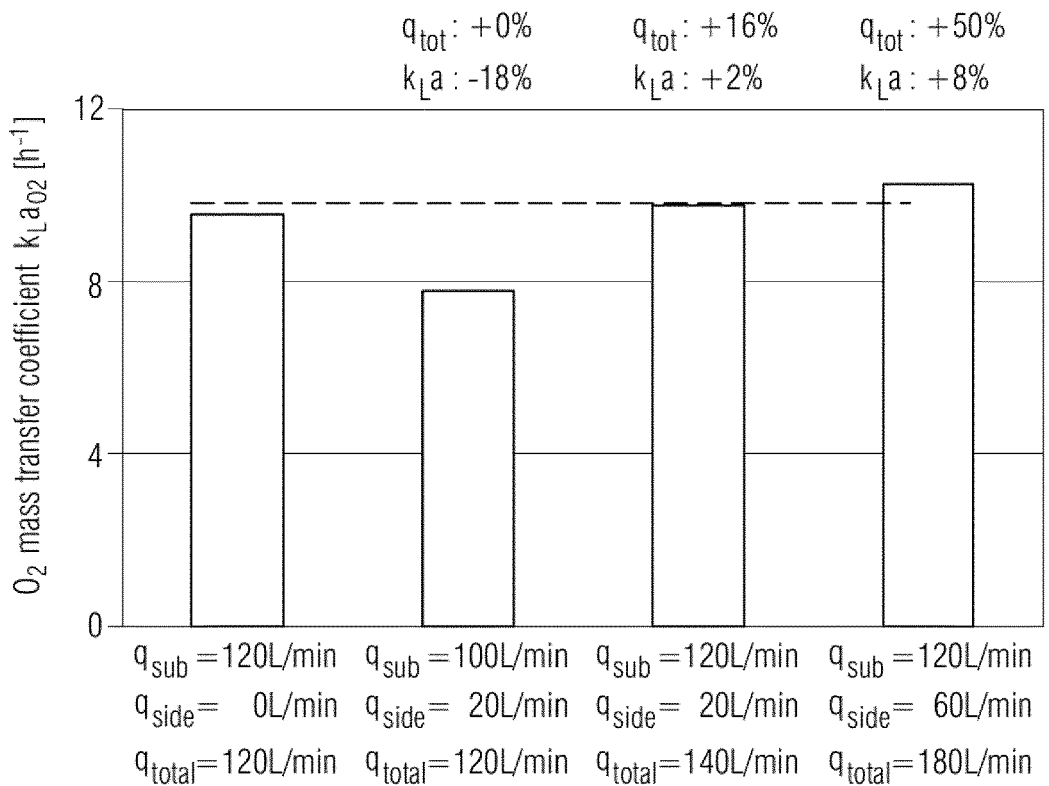
FIG. 10 is explained in the example section (Examples 2 and 3) and represents a comparison of four measurements performed to determine the mass transfer coefficient for oxygen ($k_L a_{O2}$) in dependency of the gas flow rate according to prior art as well as exemplary embodiments of the present disclosure.

For illustration purposes the results obtained in Table 1 are depicted in FIG. 10 which shows a comparison of the four measurements performed. It can be seen in FIG. 10 that a reduction of the submerse aeration by 16% in measurement 2 compared with measurement 1 has a significant influence on the mass transfer coefficient for $O_2$, even if the total aeration rate is constant in measurements 1 and 2. However, an enhancement of the side-injection by 16% in measurement 3 compared with measurement 1 shows only an increasing of the oxygen mass transfer coefficient $k_L a_{O2}$ by 2% in measurement 3 and an enhancement of 50% only by 8% in measurement 4.

The first evaluation measurements therefore confirm that the side-injection of air has only a small influence on the oxygen mass transfer performance.

Example 3: Second Evaluation Measurements

Figure 11:
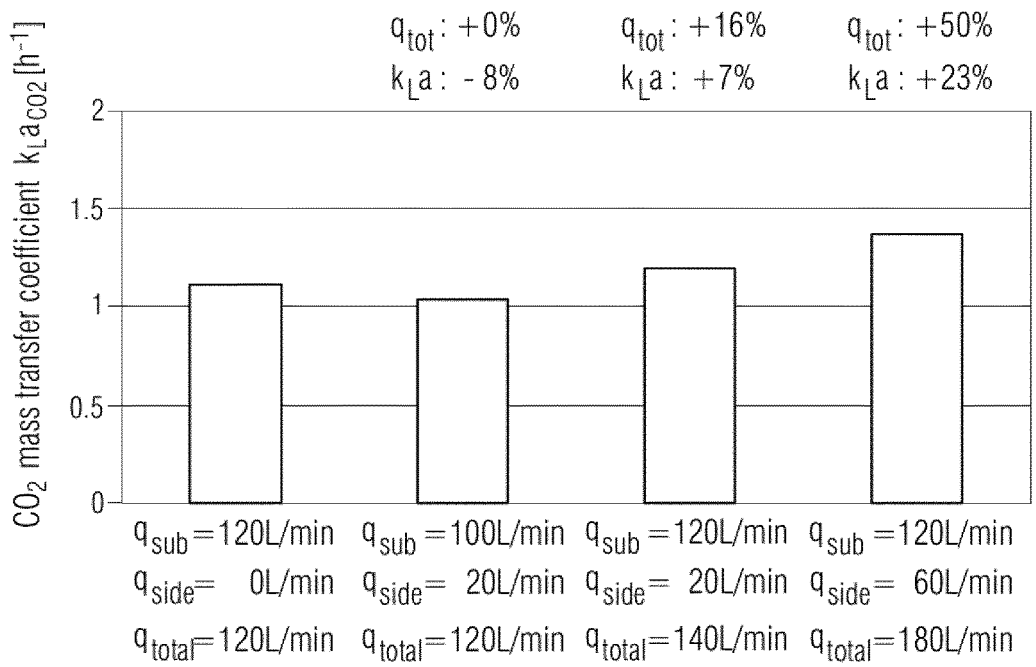
FIG. 11 is explained in the example section (Example 3) and represents a comparison of four measurements performed to determine the mass transfer coefficient for carbon dioxide ($k_L a_{CO2}$) in dependency of the gas flow rate according to prior art as well as exemplary embodiments of the present disclosure.

The same measurements as in the first evaluation measurements have been performed, but the volumetric mass transfer coefficient for carbon dioxide $k_L a_{CO2}$ has been determined (cf. FIG. 11). It can be derived from FIG. 11 that the mass transfer coefficient for carbon dioxide is increasing much stronger with increasing side-injection (up to 23% in measurement 4) compared to the mass transfer coefficient for oxygen (8%) (cf. FIG. 10).

The first and second evaluation measurements confirm that the side-injection has different influences on the mass transfer coefficient of oxygen and carbon dioxide and thus, cannot simply be added to the submersed gas flow rate. As a result, a side-injection of gas in an industrial scale aerated stirred bioreactor or fermenter enables the independent management of the oxygen concentration and the carbon dioxide concentration, respectively.

From the above described evaluations, it may be concluded that a "modified" gas flow rate exists. For a better description of the "modified" gas flow rate it can be expressed by the following equation:

$$q_{mod} = q_{sub} + C \times q_{side} \quad [1]$$

Figure 12A:
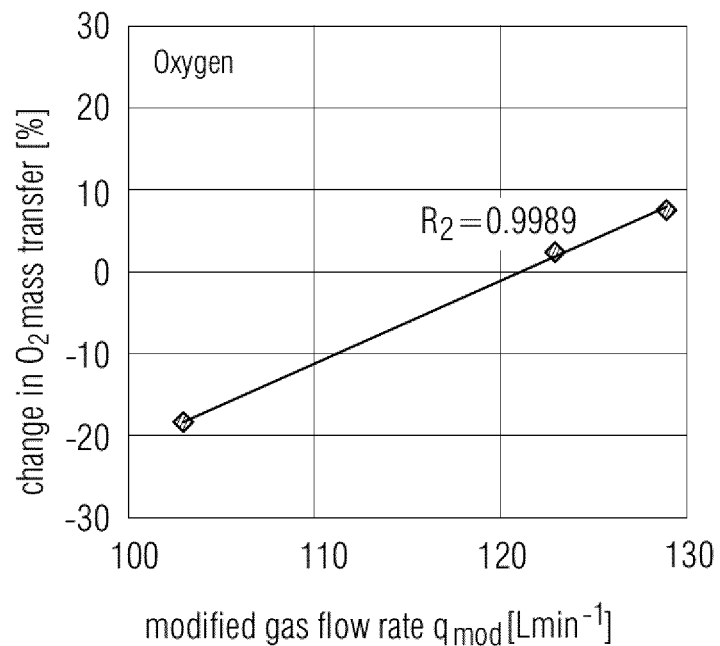
FIG. 12a is explained in the example section (Example 3) and shows the determination of an influence factor $C_{O2}$ for the mass transfer coefficient of oxygen ($k_L a_{O2}$) according to the present disclosure.
Figure 12B:
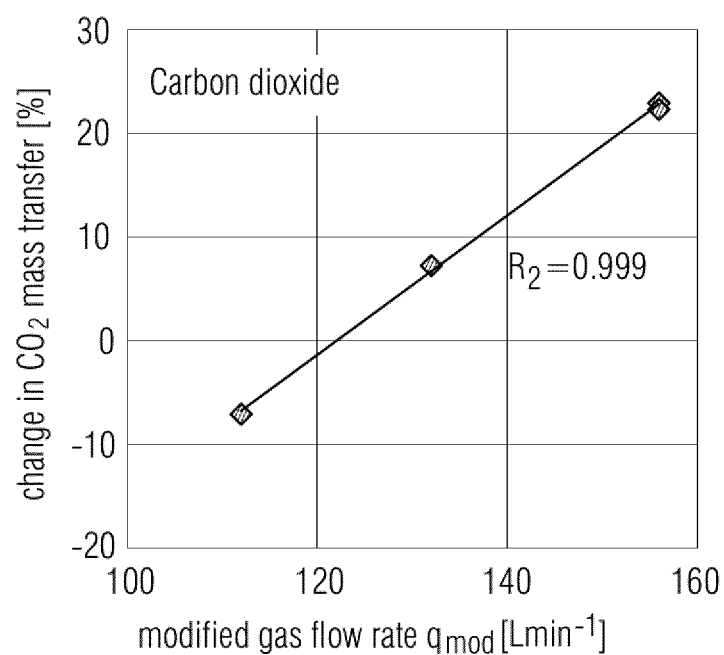
FIG. 12b is explained in the example section (Example 3) and shows the determination of an influence factor $C_{CO2}$ for the mass transfer coefficient of carbon dioxide ($k_L a_{CO2}$) according to the present disclosure.

That is a modified gas flow rate can be introduced, which includes the submerse aeration $q_{sub}$ and the side-aeration $q_{side}$ weighted with an influence factor C. The higher the factor C is, the higher is the influence of the side-aeration on the mass transfer performance. The factor C can be calculated with the assumption that the mass transfer is linear proportional to the submerse gas flow rate. This finding is illustrated in FIGS. 12a and 12b. From FIGS. 12a and 12b it can be derived that a side-injection factor of $CO_2$=0.15 can be calculated for the volumetric mass transfer coefficient of oxygen $k_L a_{O2}$ whereas the factor for carbon dioxide ($k_L a_{CO2}$) is four times higher with $C_{CO2}$=0.6.

Consequently, an additional side-injection leads to a small increase of the mass transfer performance for oxygen whereas the mass transfer performance for carbon dioxide increases significantly. Actually, a side-injection of gas leads to an increase of the mass transfer coefficient for oxygen by the factor of 0.15 only whereas the mass transfer coefficient for carbon dioxide can be enhanced by the factor of 0.6.

Example 4: Third Evaluation Measurements

The same measurements as in the first and second evaluation measurements have been performed, but different side-spargers (second spargers) have been used. Side-sparger type A has 10×3 mm drills and side-sparger type B has 32×5 mm drills. Side-sparger type B has more openings and each opening has a greater diameter compared with type A.

Figure 13A:
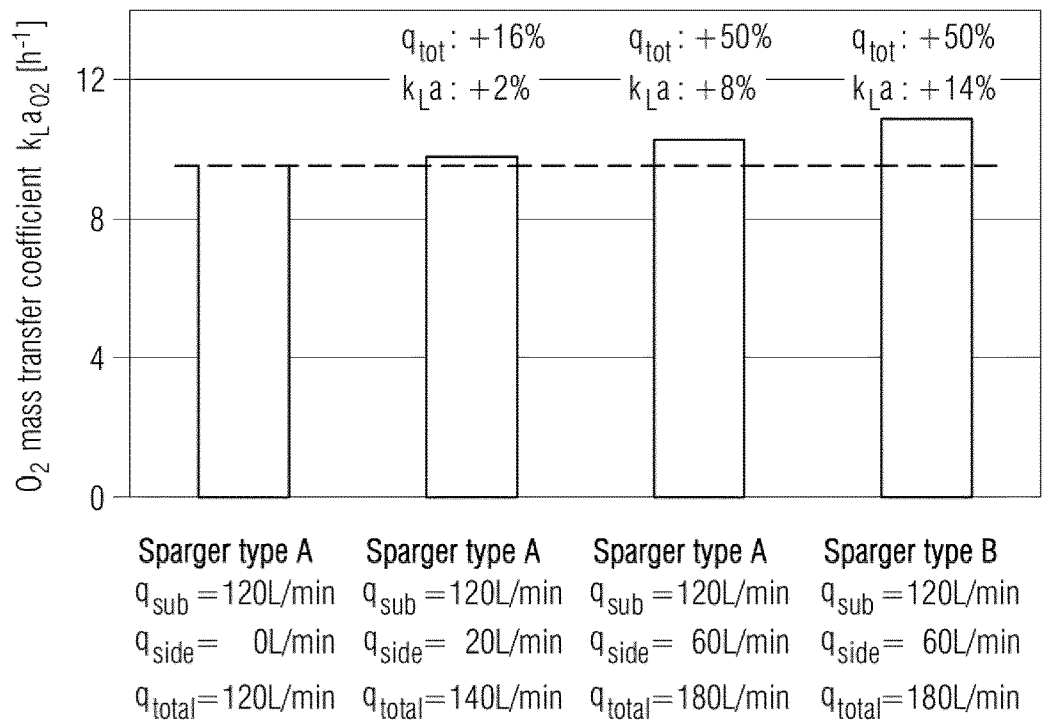
FIG. 13a is explained in the example section (Example 4) and shows a comparison of four measurements performed to determine the mass transfer coefficient for oxygen ($k_L a_{O2}$) in dependency of the gas flow rate with a side-sparger type A or a side-sparger type B according to prior art as well as exemplary embodiments of the present disclosure.
Figure 13B:
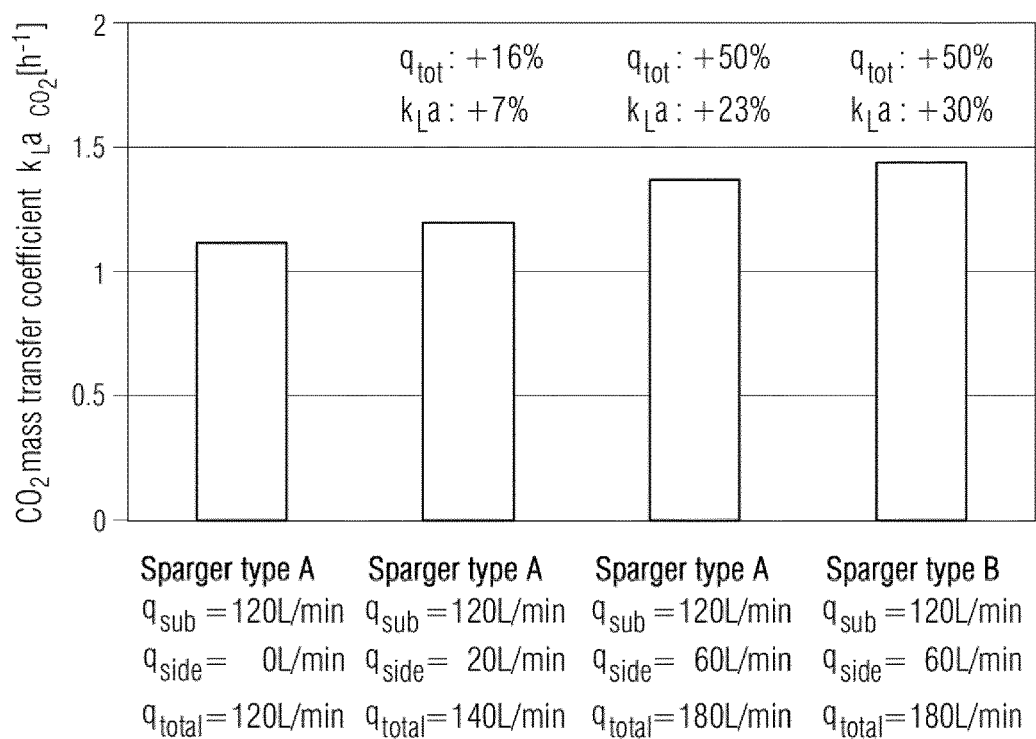
FIG. 13b is explained in the example section (Example 4) and shows a comparison of four measurements performed to determine the mass transfer coefficient for carbon dioxide ($k_L a_{CO2}$) in dependency of the gas flow rate with a side-sparger type A or a side-sparger type B according to prior art as well as exemplary embodiments of the present disclosure.

The obtained results are illustrated in FIGS. 13a and 13b. Referring to FIGS. 13a and 13b, it is confirmed that if the total gas flow rate is constant also the $CO_2$ mass transfer is almost constant. Furthermore, the side-aeration has a larger effect on the $CO_2$ mass transfer compared to the $O_2$ mass transfer. In detail, the volumetric mass transfer coefficient for carbon dioxide $k_L a_{CO2}$ of side-sparger type B is increasing much stronger with increasing side-injection (see FIG. 13b: up to 30% in measurement 4) compared to the second evaluation measurements of the mass transfer coefficient for carbon dioxide. That is, the $CO_2$ mass transfer can be further increased by selecting sparger type B.

Consequently, it is presumed that an additional side-injection of gas at a higher position with a greater number of larger gas bubbles, i.e. higher bubble rise velocities and thus a short contact time between gas and media leads to improved performance in the cell culturing process.

Example 5: Fourth Evaluation Measurements

Further measurements have been performed in order to verify the dependency of the mass transfer coefficient for carbon dioxide $k_L a_{CO2}$ and the mass transfer coefficient for oxide $k_L a_{O2}$ on the stirrer frequency and gas flow rate. The results are shown in the FIGS. 14a and 14b as well as FIGS. 15a and 15b.

In the legends to FIGS. 14a, 14b, 15a, 15b (provided at the end of the description), the results are summarized using plus signs ("+"). The plus signs in the legends have the following meaning:

+ . . . small influence
+++ . . . great influence

Figure 14A:
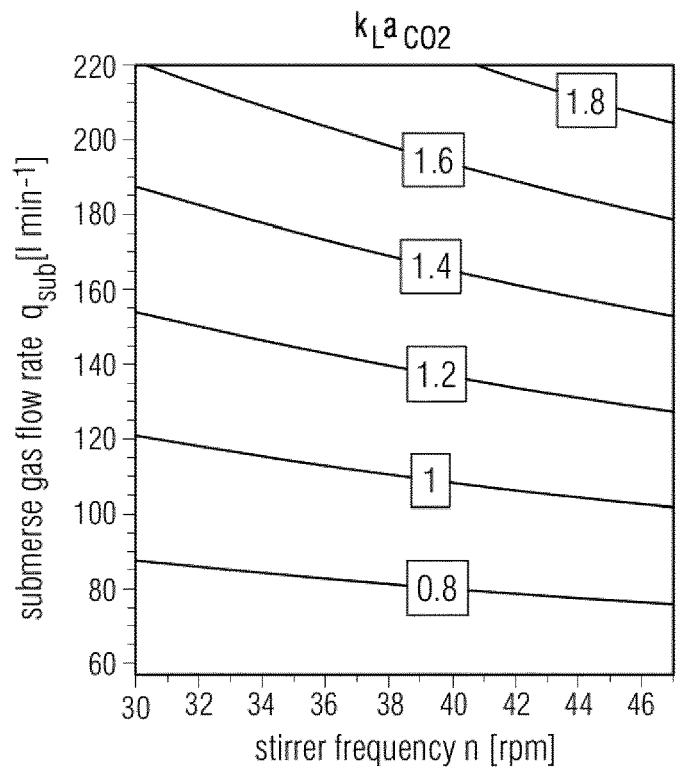
FIG. 14a is explained in the example section (Example 5) and shows measurements performed to determine the mass transfer coefficient for carbon dioxide ($k_L a_{CO2}$) in dependency of the stirrer frequency and the submerse gas flow rate.
Figure 14B:
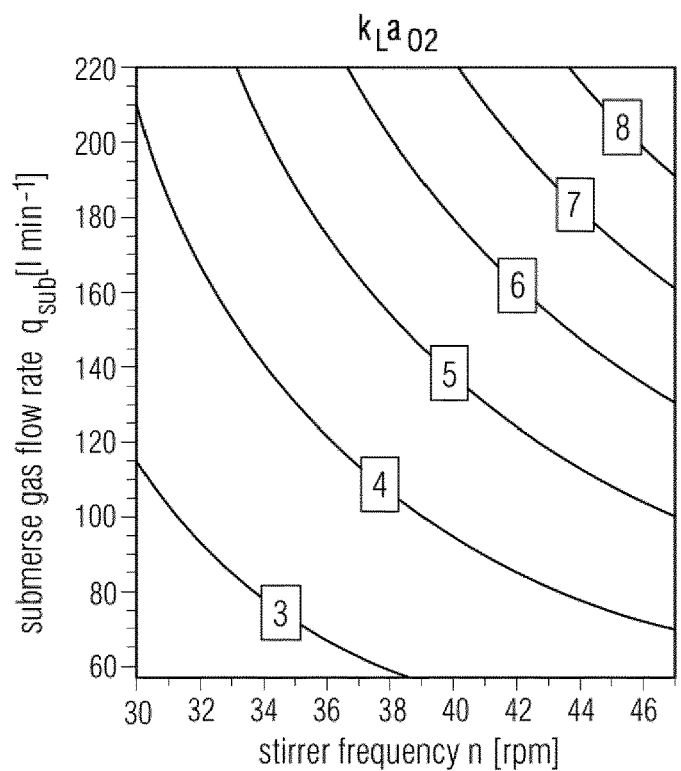
FIG. 14b is explained in the example section (Example 5) and shows measurements performed to determine the mass transfer coefficient for oxygen ($k_L a_{O2}$) in dependency of the stirrer frequency and the submerse gas flow rate.

In FIGS. 14a and 14b only one sparger is used, which is a submerse sparger located at the bottom of the vessel.

In accordance with the other experiments it has been found in FIG. 14a that the specific power input has a small influence on the mass transfer coefficient for carbon dioxide $k_L a_{CO2}$ represented by the plus sign (+) while the superficial gas flow rate has a great influence (+++) on the mass transfer coefficient for carbon dioxide $k_L a_{CO2}$.

Referring to FIG. 14b the mass transfer coefficient for oxide $k_L a_{O2}$ rises with increasing specific power input as well as increasing superficial gas flow rate.

Figure 15A:
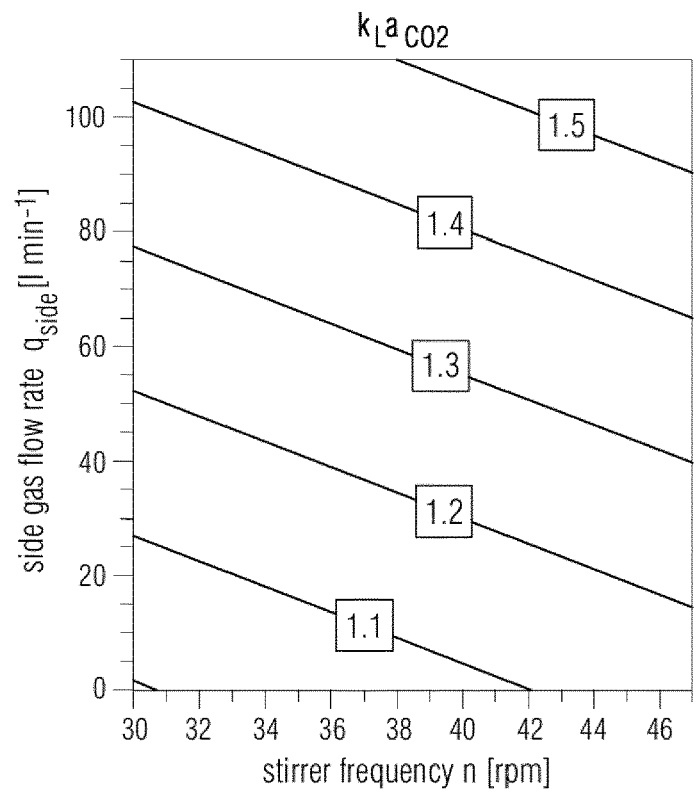
FIG. 15a is explained in the example section (Example 5) and shows measurements performed to determine the mass transfer coefficient for carbon dioxide ($k_L a_{CO_2}$) in dependency of the stirrer frequency and the side gas flow rate.
Figure 15B:
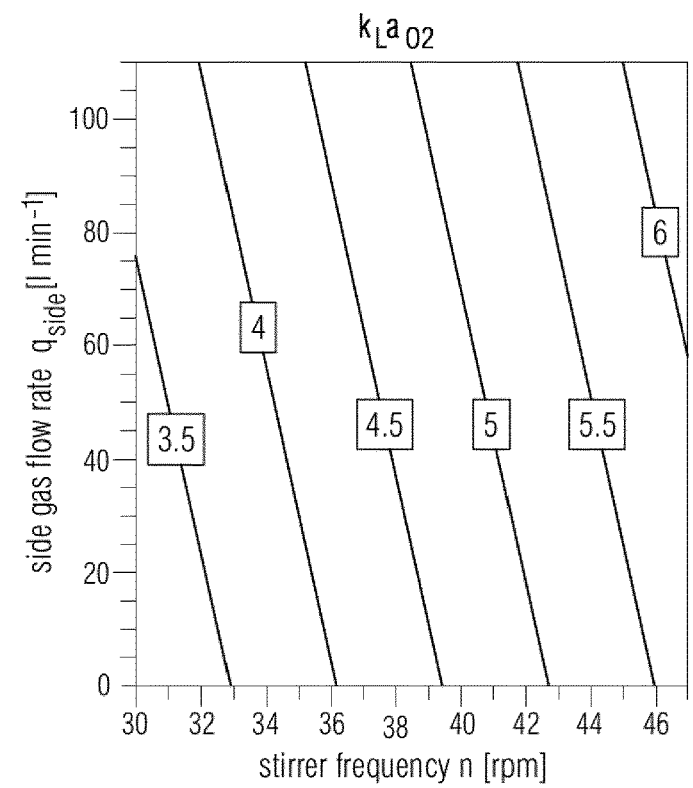
FIG. 15b is explained in the example section (Example 5) and shows measurements performed to determine the mass transfer coefficient for oxygen ($k_L a_{O_2}$) in dependency of the stirrer frequency and the side gas flow rate.

In FIGS. 15a and 15b the second sparger used is a side-sparger. In accordance with the other experiments it has been found in FIG. 15a that the specific power input has a small influence on the mass transfer coefficient for carbon dioxide $k_L a_{CO2}$ represented by the plus sign (+) whereas the superficial gas flow rate has a great influence (+++) on the mass transfer coefficient for carbon dioxide $k_L a_{CO2}$.

Referring to FIG. 15b the mass transfer coefficient for oxide $k_L a_{O2}$ rises with increasing specific power input. However, an increasing superficial gas flow rate has only a small influence on the mass transfer coefficient for oxide $k_L a_{O2}$.

Based on this approach, the independent management of carbon dioxide and oxygen in industrial scale aerated stirred bioreactors or fermenters are possible. The independent management may be based on the two principles, namely that the $CO_2$ mass transfer is almost constant if the total gas flow rate is constant and that the side-aeration has a different influence on the $CO_2$ mass transfer and the $O_2$ mass transfer.

Example 6: Evaluation of the Distance η

The distance η between the first sparger and second sparger, also designated as $η_{1,2}$, is determined by the $CO_2$ saturation concentration of the gas bubble and the time at which the gas bubble will reach the $CO_2$ saturation concentration in the bioreactor or fermenter in industrial scale. Therefore, the gas-phase residence time over the height of the reactor has been determined by the Step Response Method ("Sprungantwortmethode"), the essentials issues of this method will be explained hereinafter.

6.1. Measurement of the Gas Phase Residence Time in an Aerated Stirred Tank Reactor by the Step Response Method Only a very few publications are available dealing with the determination of the gas-phase residence time (Wachi S. and Nojima Y., Gas-Phase Dispersion in Bubble Columns, Chemical Engineering Science, Vol. 45, No. 4, pp 901-905, 1990; Yianatos J. B. and Bergh L. G., International Journal of Mineral Processing, 36 (1992), p. 81-91). The gas-phase residence time distribution in a two phase flow can be determined by means of the impulse or the step response method. However, the impulse response methods described are difficult to adapt because either radioactive or toxic tracer gases are used. Furthermore, no investigations on the gas-phase residence time distribution in aerated stirred tank reactors have been published so far. Therefore, a modified measurement technique based on the step response method to determine the gas-phase residence time is used herein.

Figure 16A:
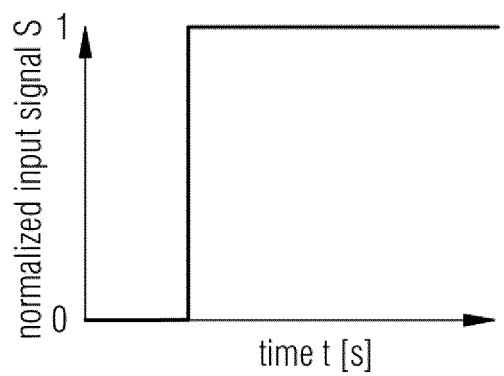
FIG. 16a is explained in the example section (Example 6) and illustrates the step response method, particularly the input to the system.
Figure 16B:
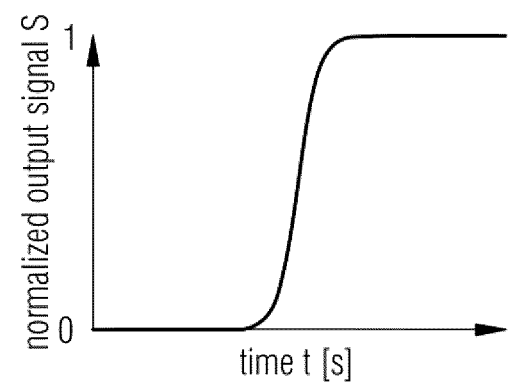
FIG. 16b is explained in the example section (Example 6) and illustrates the step response method, particularly the output of the system.

According to the control theory, the behavior of a system can be determined by either the impulse or step response method. The difference between both methods is the obtained information about the system. The residence time distribution can be determined by the impulse response method whereas the residence time by itself can be determined by the step response method. For instance, the output of the system in response to the step input is shown in FIGS. 16a and 16b. FIGS. 16a and 16b illustrate the step response method: It is shown the input to the system (FIG. 16a) and the output of the system (FIG. 16b) according to Leigh, J. R. (2004). Control Theory 2. ed., IET control engineering series, London.

As measured signal at the output of the system the radiation of a radioactive gas tracer (Yianatos J. B., Bergh, L. G., Duran, O. U., Diaz, F. J., Heresi, N. M. (1994), Measurement of Residence Time Distribution of the Gas Phase in Flotation Columns, Minerals Engineering Vol. 7, p. 333-344) or Dichlorodifluoromethane (Wachi S. and Nojima Y., loc. cit.) is used. For practical reasons, it is often not possible to use a radioactive gas tracer to realize an input impulse. Furthermore, the information about the residence time only (and not the distribution) is sufficient in the present case.

Therefore, for our application in a 12 kL acrylic glass stirred tank reactor, only the gas type is changed during the aeration to induce a step signal into the system.

Figure 17:
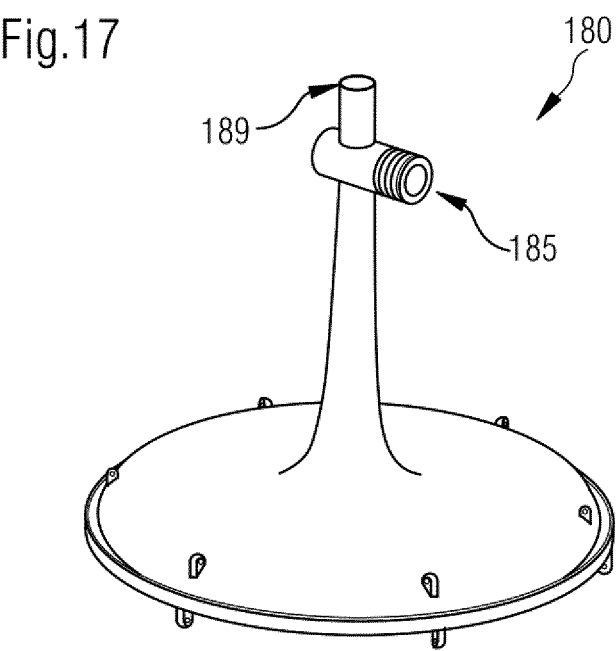
FIG. 17 is explained in the example section (Example 6) and exemplifies a bubble catcher (funnel) 180 as used in the step response measurement.

For the application of the step response method, the aerated stirred tank reactor should operate under steady process conditions, e.g. aerated, until the equilibrium in dissolved oxygen concentration is reached. During steady operation, subsequently the aeration is converted to pure nitrogen. The oxygen concentration is continuously measured at the inlet and outlet of the reactor. To minimize the effect of gas mixing within the headspace of the reactor, a funnel is installed as a "bubble catcher" on the water surface. Such a bubble catcher (funnel) 180 which minimizes the effect of the headspace of a reactor is exemplarily shown in FIG. 17. The bubble catcher (funnel) 180 is designed to take up the bubbles over a cross section and to guide the collected gas to the gas sensor. As gas sensors at the inlet and the outlet of the reactor, optical oxygen sensor spots (PreSens Precision Sensing GmbH) have been used in this case, with a very low response time of $t_{response}$<2 s. In the illustrated bubble catcher (funnel) 180 of FIG. 17 a PreSens Port 185 and an Offgas 189 are shown.

Figure 18:
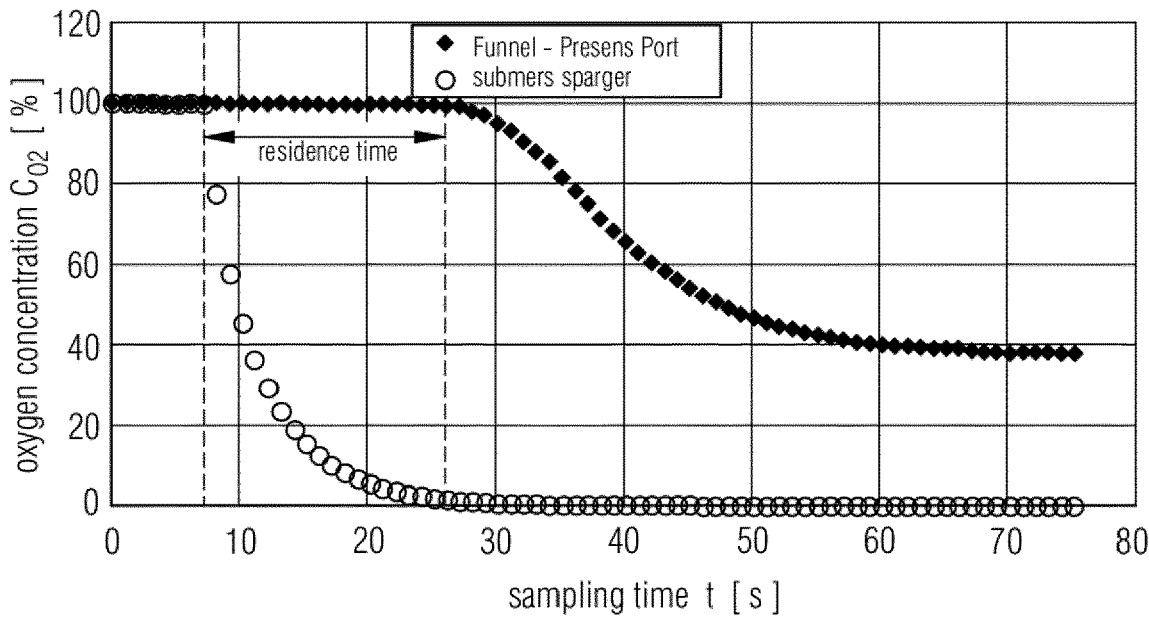
FIG. 18 is explained in the example section (Example 6) and shows a typical input and output signal from the step response method applied to a 12 kL aerated stirred tank reactor.

A typical input signal with the corresponding output signal from the step response method applied to the 12 kL aerated stirred tank reactor from the oxygen concentration at the submers sparger and the funnel, respectively, is shown in FIG. 18.

Figure 19:
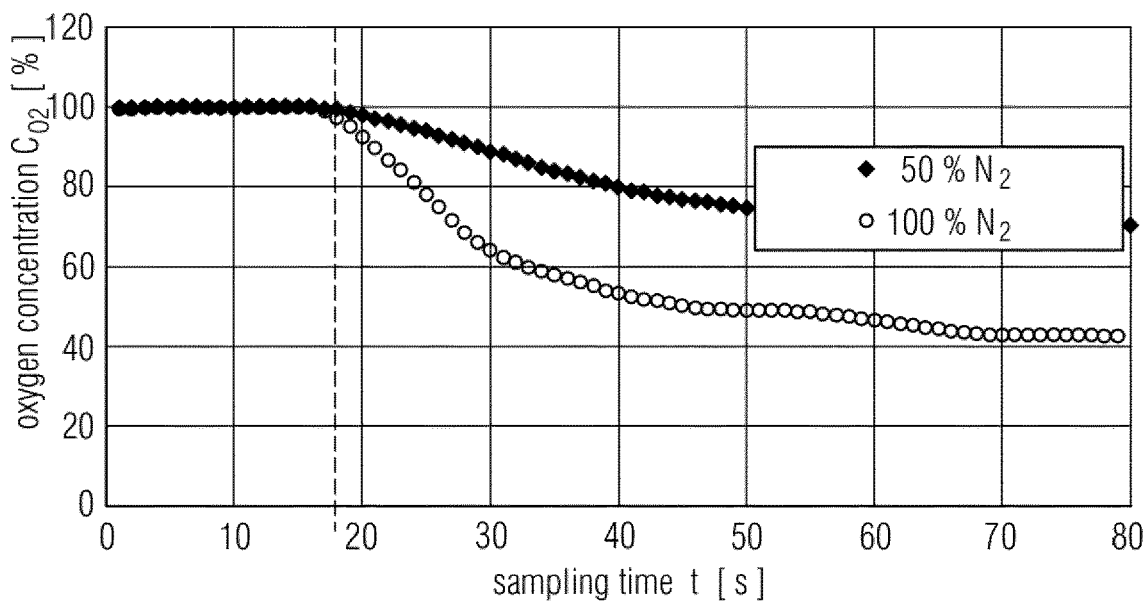
FIG. 19 is explained in the example section (Example 6) and shows a comparison of the step responses at a bubble catcher (funnel) 180 resulting from a 100% and a 50% input step.

Assuming that the residence time scale is significantly smaller than the mass transfer time scale, the gas-phase residence time is defined as time between the step input and the time at which the oxygen concentration in the exhaust air has dropped by more than 1%. This assumption can be proven by comparing the system response resulting from a 100% and a 50% step input. In FIG. 19 a comparison of the step responses at the funnel resulting from a 100% and a 50% input step are shown, respectively. Regarding FIG. 19, no difference in the response signal can be detected with regard to the time at which the output oxygen signal first drops off.

The response step method is associated with some deficiencies, which are only of minor significance in the present case for the following reasons:

The signal starts to drop, if the first bubbles are reaching the funnel. Depending on the bubble size distribution, this might happen very early (by large size bubbles) whereas the largest amount of smaller bubbles might stay much longer within the system. However, due to the use of PBS and Pluronic as solvents (phosphate-buffered saline+1 g/L Pluronic), the bubble size distribution is very narrow and the method should have an acceptable accuracy.

Under heterogeneous flow conditions it might happen, that the main bubble plume is not catched by the funnel. In this case the residence time will be overestimated.

An exchange of dissolved oxygen and nitrogen in between the oxygen and nitrogen bubbles might occur and additionally coalescence and breakup. It is assumed, that this effect can be neglected.

In summary, the step response method for determining the gas phase residence time is an easy applicable method with acceptable accuracy for the described systems and conditions.

The solvents used in the step response method was PBS (phosphate-buffered saline) and 1.0 g/L Pluronic.

Figure 20:
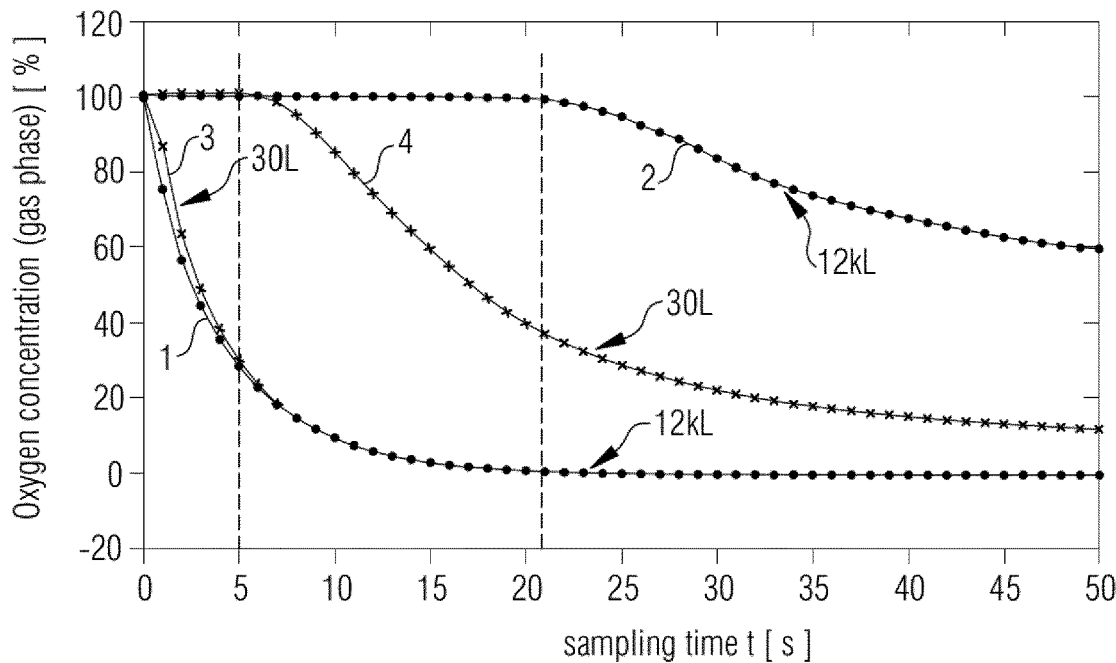
FIG. 20 is explained in the example section (Example 6) and shows the results of measurements of the gas phase residence time determined by the step function response method ("Sprungantwortmethode" as explained in the example section) in a laboratory scale bioreactor or fermenter (30 L) compared with an industrial scale bioreactor or fermenter (12,000 L)

The results of the step response method are shown in FIG. 20. In FIG. 20 the oxygen concentration in [%] is plotted against the sampling time t in [s]. A bioreactor or fermenter in laboratory scale having 30 L has been compared with a bioreactor or fermenter in an industrial scale having 12,000 L. The stirrer frequency n in [rpm] and the gas flow rate in [L h$^{-1}$] has been changed from the laboratory scale to the industrial scale in order to obtain comparable power input for each system. Therefore, the stirrer frequency for the industrial scale system is 300 rpm and the stirrer frequency for the laboratory scale is 80 rpm. The gas flow rate for the laboratory system is 1 L min$^{-1}$ and the gas flow rate for the industrial scale is 60 L min$^{-1}$.

In FIG. 20 there are shown 2 curves for the laboratory scale (30 L) and 2 curves for the industrial scale (12,000 L), respectively. The curves 1 and 2 show the measurements in industrial scale and the curves 3 and 4 show the measurements in laboratory scale. The gas concentration is measured at the gas feed at the bottom of the bioreactor or fermenter (feed) and at the top of the bioreactor or fermenter (top). As may be derived from the curves provided the residence times $t_r$ are as follows:

$$t_{r,30\,L} = 5\text{ s}$$

$$t_{r,12\,kL} = 21\text{ s}.$$

Therefore, the gas phase residence time of a bioreactor or fermenter in laboratory scale has been determined to be 5 s and the gas phase residence time for a bioreactor or fermenter in an industrial scale has been found to be 21 s.

6.2. Assessment of the $CO_2$ Mass Transfer Coefficient $k_L a_{CO2}$

The assessment of the $CO_2$ mass transfer coefficient $k_L a_{CO2}$ has been performed as follows:

Measurements for the specific gas boundary interface and volumetric $CO_2$ mass transfer coefficient $k_L a_{CO2}$ in a 2 L bioreactor or fermenter have been conducted. The results have been summarized in the following Table 2.

TABLE 2 measurement results for the specific gas boundary interface and volumetric $CO_2$-mass transfer coefficient in a 2 L bioreactor or fermenter

| Stirrer frequency n [rpm] | Gas flow rate q [L h$^{-1}$] | Specific gas boundary interface [m$^{-1}$] | volumetric $CO_2$- mass transfer coefficient $k_L a_{CO2}$ [h$^{-1}$] | $CO_2$-mass transfer coefficient $k_L a_{CO2}$ [m h$^{-1}$] |
|---|---|---|---|---|
| 140 | 10 | 0.62 | 3.05 | 4.91 |
| 140 | 15 | 0.88 | 4.02 | 4.56 |
| 140 | 20 | 1.36 | 4.89 | 3.61 |
| 200 | 10 | 0.78 | 3.68 | 4.72 |
| 200 | 15 | 1.53 | 4.86 | 3.17 |
| 240 | 10 | 0.91 | 4.06 | 4.47 |
| 240 | 15 | 1.63 | 5.35 | 3.25 |
| 240 | 20 | 1.95 | 6.51 | 3.34 |

Based on the above measurements the mass transfer coefficient of $CO_2$ has been identified in a 2 L bioreactor or fermenter to be 4±0.68 h$^{-1}$.

6.3. Estimation of the Mean Bubble Rise Velocity

Under the assumptions that the monodisperse distribution of the size of bubbles in a 12,000 L system is d=5 mm and that the carbon dioxide mass transfer coefficient $k_L a_{CO2}$=4±0.68 h$^1$ as above-mentioned also applies for the industrial scale, the theoretical carbon dioxide profile in a single bubble at 37° C. may be calculated as follows:

$$c_{CO2} = c^*_{CO2} - \exp\left(k_L a \frac{A_{bubble}}{V_{bubble}}(c_{CO2} - c^*_{CO2})t + \ln(c^*_{CO2})\right)$$

$C_{CO2}$ concentration of carbon dioxide
$C^*_{CO2}$ saturation concentration of carbon dioxide
$k_L$ mass transfer coefficient
a specific interfacial area, whereby a=A/V,
$A_{bubble}$ surface of the bubble
$V_{bubble}$ volume of the bubble
t time It can be deduced therefrom that a 95% saturation of the gas bubbles is reached after about 3.5 s.

Based on the measured mean gas phase residence time in an industrial scale bioreactor or fermenter of about 21 s and the total measured distance travelled by the bubble of 3.6 m, the mean bubble rise velocity can therefore be calculated as follows:

velocity $u$=distance/time: $u$=0.17 m/s.

As a result, after a height of about h=0.6 m (3.6 m×0.17 m/s) the gas phase is saturated with $CO_2$ and therefore no more stripping of $CO_2$ may be observed.

Since the above assessment, measurements and calculations include some evaluations and estimations the obtained result of 0.6 m is only an approximate value for the distance η which is better represented by a range such as claimed.

Comparative Example 1: A Bioreactor Comprising Only One Sparger

A proprietary BI HEX (Boehringer-Ingelheim High Expression) CHO-DG44 derived cell line expressing an antibody-like protein was cultivated in a conventional fed-batch process in a commercially available 12.000 L bioreactor for 11 days. The bioreactor comprised a Rushton and a pitched blade agitator and had a H/D (height/diameter ratio) of 2:1. The distance between the lower and the higher impeller was 1.8 m. At nominal volume the liquid height (=filling height) within the bioreactor was 4.2 m. The sparger was situated below the lowest stirrer. Growth, production and feed media derived from the proprietary BI-HEX® platform were used for this experiment. The cultivation started at 9,000 L and ended at approximately 1,100 L by the addition of feed. Throughout the process the cultivation temperature was controlled at 36.5±0.5° C., pH was kept in a range of 7±0.6 and glucose concentration in the range of 0 to 10 g/L. Oxygen supply was provided by sparging air and oxygen. The dissolved oxygen concentration was maintained at 30%.

The results are shown in the following tables A to D and depicted graphically in FIG. 21 A to D. Cells grew exponentially up to day 5 after which cell numbers stayed approximately constant. Cell viability decreased constantly during the 11 days of cultivation ending slightly below 80%. Product titer was measured from day 3 on and increased significantly until day 11. The $pCO_2$ profile of the cultivation started at around 10% and decreased steeply until day 4, after which $pCO_2$ increased again until it reached the starting value at day 11.

TABLE A

Normed viable cell growth curve. Data are given in percent of the maximum cell density reached for this run.

| Runtime [d] | Viable cell density [%] |
|---|---|
| 0 | 3 |
| 1 | 6 |
| 2 | 14 |
| 3 | 32 |
| 4 | 56 |
| 5 | 79 |
| 6 | 85 |
| 7 | 87 |
| 8 | 88 |
| 9 | 86 |
| 10 | 100 |
| 11 | 77 |

TABLE B

Cell viability

| Runtime [d] | Cell Viability [%] |
|---|---|
| 0 | 98 |
| 1 | 98 |
| 2 | 98 |
| 3 | 98 |
| 4 | 97 |
| 5 | 97 |
| 6 | 94 |
| 7 | 89 |
| 8 | 83 |
| 9 | 79 |
| 10 | 76 |
| 11 | 77 |

TABLE C

Concentration curve of the antibody derivate produced by the cells. The value is given in percent of the maximum product concentration reached in the run.

| Runtime [d] | Titer [%] |
|---|---|
| 0 | 0 |
| 1 | 0 |
| 2 | 0 |
| 3 | 6 |
| 4 | 12 |
| 5 | 21 |
| 6 | 31 |
| 7 | 45 |
| 8 | 58 |
| 9 | 73 |
| 10 | 87 |
| 11 | 100 |

TABLE D

Partial pressure of $CO_2$ within the bioreactor

| Runtime [d] | $pCO_2$ [%] |
|---|---|
| 0 | 9.9 |
| 1 | 8.5 |
| 2 | 6.6 |
| 3 | 6.1 |
| 4 | 5.5 |
| 5 | 6.9 |
| 6 | 7.9 |
| 7 | 8.5 |
| 8 | 8.7 |
| 9 | 9.0 |
| 10 | 9.2 |
| 11 | 9.9 |

Figure 21:
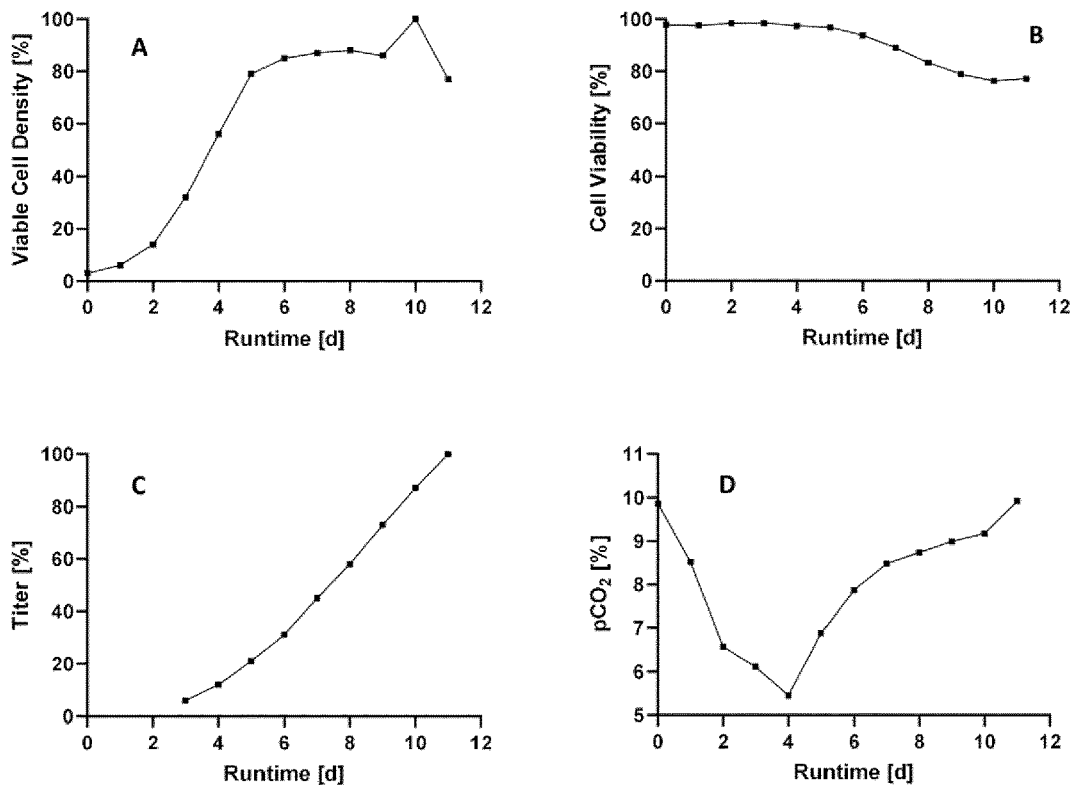
FIG. 21 is explained in the example section (Comparative Example 1) and shows the results of the viable cell density, cell viability, titer and partial pressure of $CO_2$ of the culturing of an antibody-derivative in a conventional fed-batch process in a commercially available 12.000 l bioreactor for 11 days whereby the bioreactor comprises only one sparger.

The results of the tables A to D above are illustrated in FIG. 21. The figure shows cultivation data from the exemplary 12,000 L manufacturing run according to Comparative Example 1. In (A) the normed viable cell growth curve is given for the 11 days of cultivation. Data is given in percent of the maximum cell density reached in this run. In (B) the cell viability for the cultivation is depicted. (C) shows the concentration curve of the antibody derivate produced by the cells. The value is given in percent of the maximum product concentration reached in the run. In (D) the partial pressure of $CO_2$ within the bioreactor is given.

Example 7: A Bioreactor Comprising a First Sparger and a Second Sparger

Experiments according to Comparative Example 1 can be performed but instead of only one sparger two spargers can be used, as according to the invention. The first sparger can be situated below the lowest stirrer and can be a central or a side sparger. The second sparger can be located at a position in the bioreactor or fermenter above the first sparger in a distance η whereby η is selected to be in the range from at least about 0.4 m to at most about 0.5 m below the filling height of the bioreactor or fermenter. The second sparger is a central or a side sparger.

The presence of the two spargers in the bioreactor increases the area in the liquid medium where $CO_2$-stripping will take place. If the second sparger is placed near the surface of the liquid, e.g. about 0.5 m below the filling height of the bioreactor or fermenter, it may strip the area downstream while the first sparger being placed near the bottom of the bioreactor may strip the area upstream of the liquid medium. In sum, the full filling height of the bioreactor or fermenter is subjected to a $CO_2$-stripping.

It can be expected that the presence of a second sparger which is located above a first sparger in the distance η which is selected in the range as indicated above will have a significant impact on the $CO_2$-stripping. That is, a decrease of the partial pressure of $CO_2$ in the culture (liquid medium) of the bioreactor by at least about 0.5%, or at least about 1% or at least about 2% up to about 20% can be presumed compared with the embodiment of Comparative Example 1.

Furthermore, a higher product titer and a higher product yield compared to Comparative Example 1 will be expected. The concentration of an antibody or an antibody derivate produced by the cells can be presumed to be increased by at least about 1% or at least about 5% or at least about 10% up to about 30% compared with the embodiment of Comparative Example 1.

Also small improvements in a process commercially used on a large scale as in the present case such as at least about 0.5% or at least about 1% represent a meaningful contribution. Even small improvements of the process such as the stripping performance and the yield are very relevant improvements in large-scale production and have to be regarded as significant.

In case the second sparger is selected to be a side sparger it can be expected that the advantageous technical effects as disclosed herein, particularly the decrease of the partial pressure of $CO_2$ in the culture (liquid medium) of the bioreactor and the increase of the product titer will be more prominent, respectively.

Example 8: Variation of the Distance η Between the First Sparger and the Second Sparger Experiments according to example 7 can be performed wherein the distance η between the first sparger and the second sparger will be varied. The first sparger can be situated below the lowest stirrer; the second sparger can be located at a position in the bioreactor or fermenter above the first sparger in a distance η. The second sparger is located above the first sparger in a distance η which is about ⅔ of the filling height of the bioreactor or fermenter, about ½ of the filling height of the bioreactor or fermenter, about 3.0 m, about 2.9 m, about 2.8 m, about 2.7 m, about 2.6 m, about 2.5 m, about 2.4 m, about 2.3 m, about 2.2 m, about 2.1 m, about 2.0 m, about 1.9 m, about 1.8 m, about 1.7 m, about 1.6 m, about 1.5 m, about 1.4 m, about 1.3 m, about 1.2 m, about 1.1 m, about 1.0 m, about 0.95 m, about 0.90 m, about 0.85 m, about 0.80 m, about 0.75 m, about 0.70 m, about 0.65, about 0.6 m, about 0.55, about 0.45 and about 0.4 m.

The presence of the two spargers in the bioreactor increases the area in the liquid medium where $CO_2$-stripping will take place. The second sparger may be placed in a distance η whereby η can be selected so that the areas where $CO_2$-stripping is performed by the first and the second sparger overlap to a certain extent.

Therefore, it can be expected that the presence of a second sparger which is located above a first sparger in the distance η having one of the above-mentioned values will have a significant impact on the $CO_2$-stripping. That is, a decrease of the partial pressure of $CO_2$ in the culture (liquid medium) of the bioreactor by at least about 0.5%, or at least about 1% or at least about 2% up to about 20% can be presumed compared with the embodiment of Comparative Example 1.

Furthermore, a higher product titer and a higher product yield compared to Comparative Example 1 can be expected. The concentration of an antibody derivate produced by the cells can be presumed to be increased by at least about 1% or at least about 5% or at least about 10% up to about 30% compared with the embodiment of Comparative Example 1.

Also small improvements in a process commercially used on a large scale as in the present case such as at least about 0.5% or at least about 1% represent a meaningful contribution. Even small improvements of the process such as the stripping performance and the yield are very relevant improvements in large-scale production and have to be regarded as significant.

In case the second sparger is selected to be a side sparger it can be expected that the advantageous technical effects as disclosed herein, particularly the decrease of the partial pressure of $CO_2$ in the culture (liquid medium) of the bioreactor and the increase of the product titer will be more prominent, respectively.

Comparative Example 2: A Bioreactor Comprising Two Spargers but the Distance η is Outside of the Claimed Range Experiments according to example 7 can be performed wherein the distance η between the first sparger and the second sparger is outside the claimed range. In detail, the distance η is lower than 0.4 m, such as 0.35 m or 0.3 m or 0.2 m or 0.1 m. It can be expected that the technical effects due to the presence of the second sparger will not be achieved, i.e. the advantages resulting from a decrease of the partial pressure of $CO_2$ in the culture (liquid medium) of the bioreactor and a higher product titer and a higher product yield will not be obtained. The positive effects of two spargers present at the same time in the bioreactor do not occur. Actually, the performance of the bioreactor will approach to a bioreactor having only one sparger as described in Comparative Example 1. Therefore, the lower value of 0.4 m can be considered to be a critical value.

Figure 2:
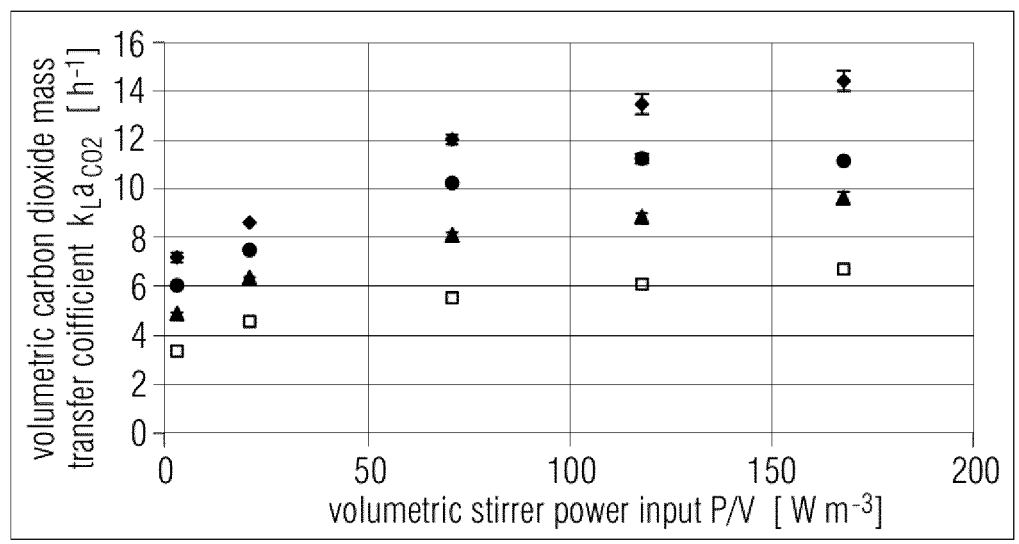
FIG. 2 shows the volumetric mass transfer coefficient for carbon dioxide $k_L a_{CO2}$ in dependency of the volumetric stirrer power input P/V for different superficial gas velocities $w^0_g$ on laboratory scale.
Figure 3:
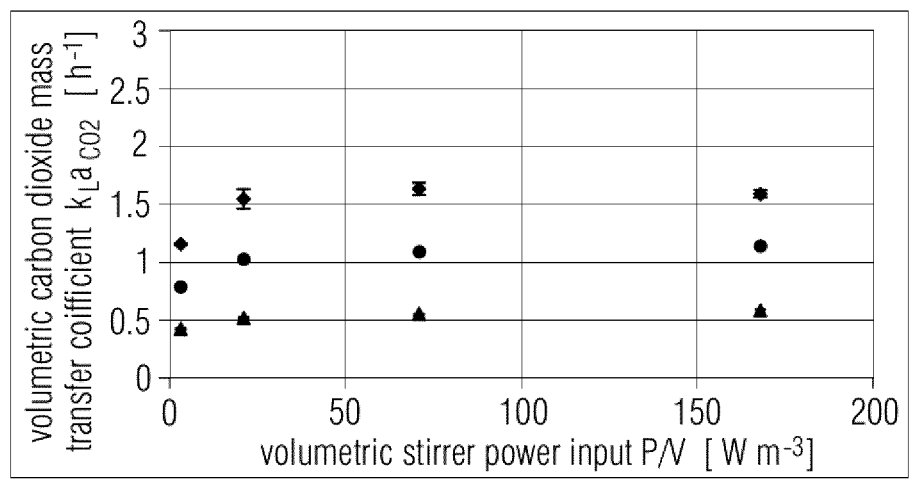
FIG. 3 shows the volumetric mass transfer coefficient for carbon dioxide $k_L a_{CO2}$ in dependency of the volumetric stirrer power input P/V for different superficial gas velocities $w^0_g$ on industrial scale.
Figure 4:
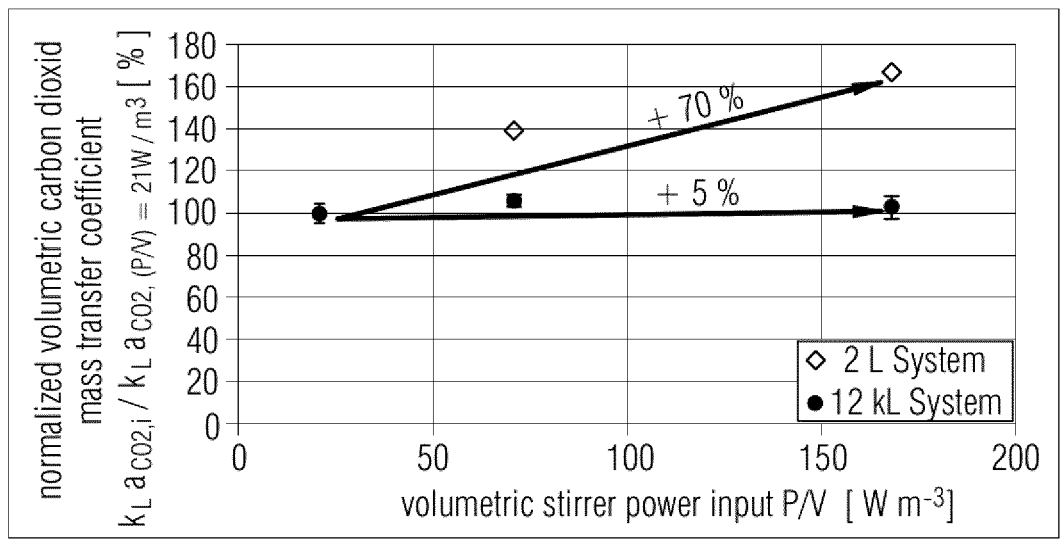
FIG. 4 shows the comparison of the mass transfer coefficients for carbon dioxide $k_L a_{CO2}$ between laboratory and industrial scales based on the values obtained in FIGS. 2 and 3.

LIST OF REFERENCE SIGNS 10, 10.1, 10.2, 10.3 bubble(s) from the first sparger
20, 20.1, 20.2, 20.3 bubble(s) from the second sparger
100 bioreactor or fermenter
102 vessel
105 bottom portion
110 sidewall
120 stirrer
140 gas supply tube
150 first sparger
160 second sparger
170 third sparger
180 bubble catcher (funnel)
185 PreSens Port
189 Offgas
A central axis
$r_s$ stirrer radius
$d_s$ stirrer diameter
d1, d2 distance defined by the stirrer radius $r_s$
D diameter of the bioreactor or fermenter
R1, R2, R3, R4 stirrers
η distance between two spargers
$η_{1,2}$ distance between first sparger and second sparger
$η_{2,3}$ distance between second sparger and third sparger
$η_{3,4}$ distance between third sparger and fourth sparger
Legends to Some of the Figures:
FIG. 2:
◆ $w^0_g$=0.96 mm s$^{-1}$
● $w^0_g$=0.75 mm s$^{-1}$ ▲ $w^0_g$=0.53 mm s$^{-1}$
□ $w^0_g$=0.32 mm s$^{-1}$
Mass Transfer Measurements:
System: 0.9% NaCl—water/air
Stirrer: Rushton/Pitched blade
Volume: 2 L
Temperature: 37° C.
FIG. 3:
♦ $w^0_g$=0.95 mm s$^{-1}$
● $w^0_g$=0.64 mm s$^{-1}$
▲ $w^0_g$=0.32 mm s$^{-1}$
Mass Transfer Measurements:
System: 0.9% NaCl—water/air
Stirrer: Rushton/Pitched blade
Volume: 12000 L
Temperature: 37° C.
FIG. 4:
Mass Transfer Measurements:
System: 0.9% NaCl—water/air
Stirrer: Rushton/Pitched blade
Superficial gas velocity: 0.96 mm s$^{-1}$
Volume: 12000 L and 2 L
Temperature: 37° C.

---

Fig. 14a:

| Specific power input | + | } $k_La_{CO2}$ +++ |
|---|---|---|
| Superficial gas flowrate | +++ | |

Fig. 14b:

| Specific power input | +++ | } $k_La_{O2}$ +++ |
|---|---|---|
| Superficial gas flowrate | +++ | |

Fig. 15a:

| Specific power input | + | } $k_La_{CO2}$ +++ |
|---|---|---|
| Superficial gas flowrate | +++ | |

Fig. 15b:

| Specific power input | +++ | } $k_La_{O2}$ +++ |
|---|---|---|
| Superficial gas flowrate | + | |

Fig. 18:
Residence Time Measurements:
Filling Volume: 12 m$^3$
Stirrer: Rushton/Pitched blade
Stirrer frequency: 60 rpm
Gas flow rate: 60 L/min
Medium: DI-Water
Temperature: T = 37° C.
Fig. 19:
Residence Time Measurements:
Filling Volume: 12 m$^3$
Stirrer: Rushton/Pitched blade
Stirrer frequency: 60 rpm
Gas flow rate: 60 L/min
Medium: DI-Water
Temperature: T = 37° C.

-continued

Fig. 20:
-1- n = 300 rpm/q = 1|min$^{-1}$ Feed
-2- n = 300 rpm/q = 1|min$^{-1}$ Top
-3- n = 80 rpm/ = 60|min$^{-1}$ Feed
-4- n = 80 rpm/q = 60|min$^{-1}$ Top

The invention claimed is:

1. A bioreactor or fermenter (100) for the culturing of cells or microorganisms in suspension in a liquid medium in industrial scale comprising:
a vessel (102) containing the culture in a liquid medium having a determined filling height;
a stirrer (120) provided in the vessel to stir the liquid medium;
a first sparger (150) arranged in the bottom portion (105) of the vessel (102) provided to supply gas bubbles (10, 10.1, 10.2, 10.3) continuously to the liquid medium, the gas being selected from air and oxygen gas; and
a second sparger (160) arranged in the vessel (102) and provided above the first sparger (150) to supply additional air bubbles and/or additional oxygen gas bubbles (20, 20.1, 20.2, 20.3) continuously to the liquid medium;
wherein the second sparger (160) is located at a position in the bioreactor or fermenter (100) above the first sparger (150) in a distance η, wherein η is selected to be in the range from at least about 0.4 m above the first sparger (150) to at most about 0.5 m below the filling height of the bioreactor or fermenter (100) or
about 0.4 m above the first sparger to about ⅔ of the filling height of the bioreactor or fermenter (100) or
about 0.4 m to about 3.0 m above the first sparger.

2. The bioreactor or fermenter (100) according to claim 1, wherein the bioreactor or fermenter (100) comprises a filling height in the range from about 8 to about 20 m.

3. The bioreactor or fermenter (100) according to claim 1, wherein the second sparger (160) is a side-sparger.

4. The bioreactor or fermenter (100) according to claim 1, wherein a third sparger (170) and one or more optional further sparger(s) are provided in the bioreactor or fermenter (100) above the first sparger (150) and the second sparger (160), wherein the distance between two consecutive spargers (150, 160) (160, 170), one arranged above the other, is selected to be η.

5. The bioreactor or fermenter (100) according to claim 1, wherein the stirrer (120) has a stirrer radius $r_s$ which is located around a central axis A through the bioreactor or fermenter (100), wherein the first sparger (150) is arranged at a distance from the central axis A of the bioreactor or fermenter (100) such that the gas bubbles (10, 10.1, 10.2, 10.3) provided enter the liquid medium at a distance which is equal to or less than the stirrer radius $r_s$; and/or
wherein the second sparger (160) is arranged at a distance from the central axis A such that the bubbles (20, 20.1, 20.2, 20.3) provided enter the liquid phase at a distance which is larger than the stirrer radius $r_s$.

6. The bioreactor or fermenter (100) according to claim 1, wherein one or more additional stirrer(s) (R2, R3, R4) is(are) provided in addition to the stirrer (120, R1), the additional stirrer(s) (R2, R3, R4) being located above and/or below the second sparger (160).

7. The bioreactor or fermenter (100) according to claim 1, wherein the first sparger (150) and the second sparger (160) are static spargers selected from tube type spargers, open-tube spargers, sintering plates, perforated slabs, ring spargers, spider type spargers, disc type spargers, sheet type spargers, cup type spargers, and bushing type spargers.

8. The bioreactor or fermenter (100) according to claim 1, wherein the first sparger (150) is a central sparger or a side sparger and the second sparger (160) is a side-sparger.

9. A process comprising culturing cells or microorganisms in a bioreactor or fermenter (100) according to claim 1, wherein a second sparger (160), an optional third sparger (170) and one or more optional further sparger(s) are provided in the bioreactor or fermenter (100) to promote the growth, viability, productivity and/or any other metabolic condition of the cells or microorganisms to be cultivated.

10. A process comprising providing a second sparger (160), an optional third sparger (170) and one or more optional further sparger(s) in a bioreactor or fermenter (100) according to claim 1, wherein the spargers (160, 170) are provided in the bioreactor or fermenter (100) to promote the growth, viability, productivity and/or any other metabolic condition of cells or microorganisms to be cultivated in the bioreactor or fermenter (100).

11. A process to control and adjust the content of dissolved $CO_2$ and the content of dissolved $O_2$ in a liquid medium in a bioreactor or fermenter (100) for the culturing of cells or microorganisms in suspension in industrial scale, said method comprising:
providing a vessel (102) containing the culture in a liquid medium;
stirring the liquid medium;
continuously supplying gas bubbles (10, 10.1, 10.2, 10.3) from a first sparger (150) arranged in the bottom portion (105) of the vessel (102) to the liquid medium, the gas being selected from air and oxygen gas;
continuously supplying gas bubbles (20, 20.1, 20.2, 20.3) from a second sparger (160) arranged in the vessel (102) to the liquid medium, the gas being selected from air and/or oxygen gas, wherein the second sparger (160) is arranged above the first sparger (150) and the second sparger (160) is a side-sparger; and
selecting and adjusting a modified gas flow rate $q_{mod}(O_2)$ and selecting and adjusting a modified gas flow rate $q_{mod}(CO_2)$ which are both suitable for the culturing process, based on the gas flow rate $q_{sub}$ of the submerse or first sparger (150) and the gas flow rate $q_{side}$ of the side or second sparger (160), wherein the following equations apply:

$$q_{mod}(O_2) = q_{sub} + C_{O2} \times q_{side} \quad [1a]$$

and $$q_{mod}(CO_2) = q_{sub} + C_{CO2} \times q_{side} \quad [1b]$$

wherein
$q_{sub}$ represents the gas flow rate of the submerse or first sparger (150);
$q_{side}$ represents the gas flow rate of the side or second sparger (160);
$C_{O2}$ represents an influence factor C of the volumetric oxygen mass transfer, wherein $C_{O2} = 0.15$; and
$C_{CO2}$ represents an influence factor C of the volumetric carbon dioxide mass transfer, wherein $C_{CO2} = 0.6$.

12. The process according to claim 11, wherein $q_{sub}$ is adjusted to be greater than $q_{side}$.

13. The process according to claim 11, wherein the position of the second sparger (160) in the bioreactor or fermenter (100) is selected to be above the first sparger (150) in a distance η, wherein η is selected to be in the range from at least about 0.4 m above the first sparger (150) to at most about 0.5 m below the filling height of the bioreactor or fermenter (100) or
about 0.4 m above the first sparger to about ⅔ of the Filling Height of the Bioreactor or fermenter (100) or
about 0.4 m to about 3.0 m above the first sparger.

14. The process according to claim 11, wherein a third sparger (170) and one or more optional further sparger(s) are provided in the bioreactor or fermenter (100) above the first sparger (150) and second sparger (160), wherein the distance between two consecutive spargers (150, 160) (160, 170), one arranged above the other, is selected to be n.

15. The process according to claim 11, wherein the stirrer (120) has a stirrer radius $r_s$ which is located around a central axis A through the bioreactor or fermenter (100),
wherein the first sparger (150) is arranged at a distance from the central axis A of the bioreactor or fermenter (100) such that the gas bubbles (10, 10.1, 10.2, 10.3) provided enter the liquid medium at a distance which is equal to or less than the stirrer radius $r_s$;
and/or
wherein the second sparger (160) is arranged at a distance from the central axis A such that the bubbles (20, 20.1, 20.1, 20.3) provided enter the liquid phase at a distance which is larger than the stirrer radius $r_s$.

16. The process according to claim 11, wherein one or more additional stirrer(s) (R2, R3, R4) is(are) provided in addition to the first stirrer (120, R1), the additional stirrer(s) (R2, R3, R4) being located above and/or below the second sparger (160).

17. The process according to claim 11, wherein the first sparger (150) is a central sparger or a side sparger and the second sparger (160) is a side-sparger.

18. The process according to claim 11, wherein the first sparger (150) and the second sparger (160) are static spargers selected from spargers with a pipe-geometry, tube type spargers, open-tube spargers, sintering plates, perforated slabs, ring spargers, spider type spargers, disc type spargers, sheet type spargers, cup type spargers, and bushing type spargers.

* * * * *